(12) United States Patent
Francis et al.

(10) Patent No.: US 9,448,755 B2
(45) Date of Patent: Sep. 20, 2016

(54) WEARABLE ELECTRONIC DEVICE HAVING HETEROGENEOUS DISPLAY SCREENS

(71) Applicant: Intel Corporation, Santa Clara, CA (US)

(72) Inventors: Mark R. Francis, Portland, OR (US); Mark Pontarelli, Lake Oswego, OR (US); Andy S. Idsinga, Portland, OR (US); Katherine Niedermeyer, Hillsboro, OR (US); Katherine M. Dill, San Francisco, CA (US); Erin M. Muntzert, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 99 days.

(21) Appl. No.: 14/142,841

(22) Filed: Dec. 28, 2013

(65) Prior Publication Data
US 2015/0186092 A1  Jul. 2, 2015

(51) Int. Cl.
*G06F 1/16* (2006.01)
*G06F 3/14* (2006.01)
(Continued)

(52) U.S. Cl.
CPC ............ *G06F 3/1423* (2013.01); *G06F 1/163* (2013.01); *G06F 1/1637* (2013.01); *G06F 3/017* (2013.01); *G06F 3/048* (2013.01); *G06F 3/147* (2013.01); *G06T 1/20* (2013.01)

(58) Field of Classification Search
CPC ...................................................... G06F 1/163
USPC ........................................................ 345/520
See application file for complete search history.

(56) References Cited

U.S. PATENT DOCUMENTS 8,249,547 B1   8/2012  Fellner
8,712,383 B1*  4/2014  Hayes et al. ............... 455/412.2
(Continued)

FOREIGN PATENT DOCUMENTS

JP    2003-70017    3/2003
JP    2004-62052    2/2004
(Continued)

OTHER PUBLICATIONS

International Search Report and Written Opinion in International Application No. PCT/US2014/072254, mailed on Apr. 20, 2015, 7 pages.
(Continued)

*Primary Examiner* — Jacinta M Crawford
*Assistant Examiner* — Shivang Patel
(74) *Attorney, Agent, or Firm* — Patent Capital Group

(57) ABSTRACT

Particular embodiments described herein provide for a wearable electronic device, such as a bracelet, watch, wristband or armband. One particular example implementation of a wearable electronic device may include a first display screen, a second display screen, and logic. At least a portion of the logic is implemented in hardware. The logic is configured to receive a communication over a wireless network, and to display, in the first display screen, a communication alert. The communication alert can be a graphic design. The logic is also configured to receive input data indicative of a screen transition input to view information associated with the communication, and to display, in the second display screen, the information associated with the communication. In further embodiments, the graphic design includes a notification pattern indicating one or more attributes of the communication. In further embodiments, the first and second display screens form a single display screen.

24 Claims, 17 Drawing Sheets

(51) Int. Cl.
*G06T 1/20* (2006.01)
*G06F 3/048* (2013.01)
*G06F 3/147* (2006.01)
*G06F 3/01* (2006.01)

(56) References Cited

U.S. PATENT DOCUMENTS

| | | |
|---|---|---|
| 2005/0128214 A1 | 6/2005 | Tseng |
| 2009/0135369 A1 | 5/2009 | Burnstein |
| 2011/0157046 A1* | 6/2011 | Lee et al. .................. 345/173 |
| 2012/0173631 A1* | 7/2012 | Yoakum et al. ............. 709/206 |
| 2012/0253485 A1* | 10/2012 | Weast et al. ................. 700/91 |
| 2013/0135108 A1 | 5/2013 | Alameh et al. |
| 2013/0331058 A1 | 12/2013 | Harvey |
| 2014/0053315 A1 | 2/2014 | Pond et al. |
| 2015/0187327 A1 | 7/2015 | Francis et al. |

FOREIGN PATENT DOCUMENTS

| | | |
|---|---|---|
| JP | 2007-47594 | 2/2007 |
| WO | WO 2015/100371 A1 | 7/2015 |

OTHER PUBLICATIONS

USPTO Aug. 17, 2015 Nonfinal Rejection in U.S. Appl. No. 14/142,796, 16 pages.
USPTO Jan. 12, 2016 Final Rejection in U.S. Appl. No. 14/142,796, 19 pages.

* cited by examiner

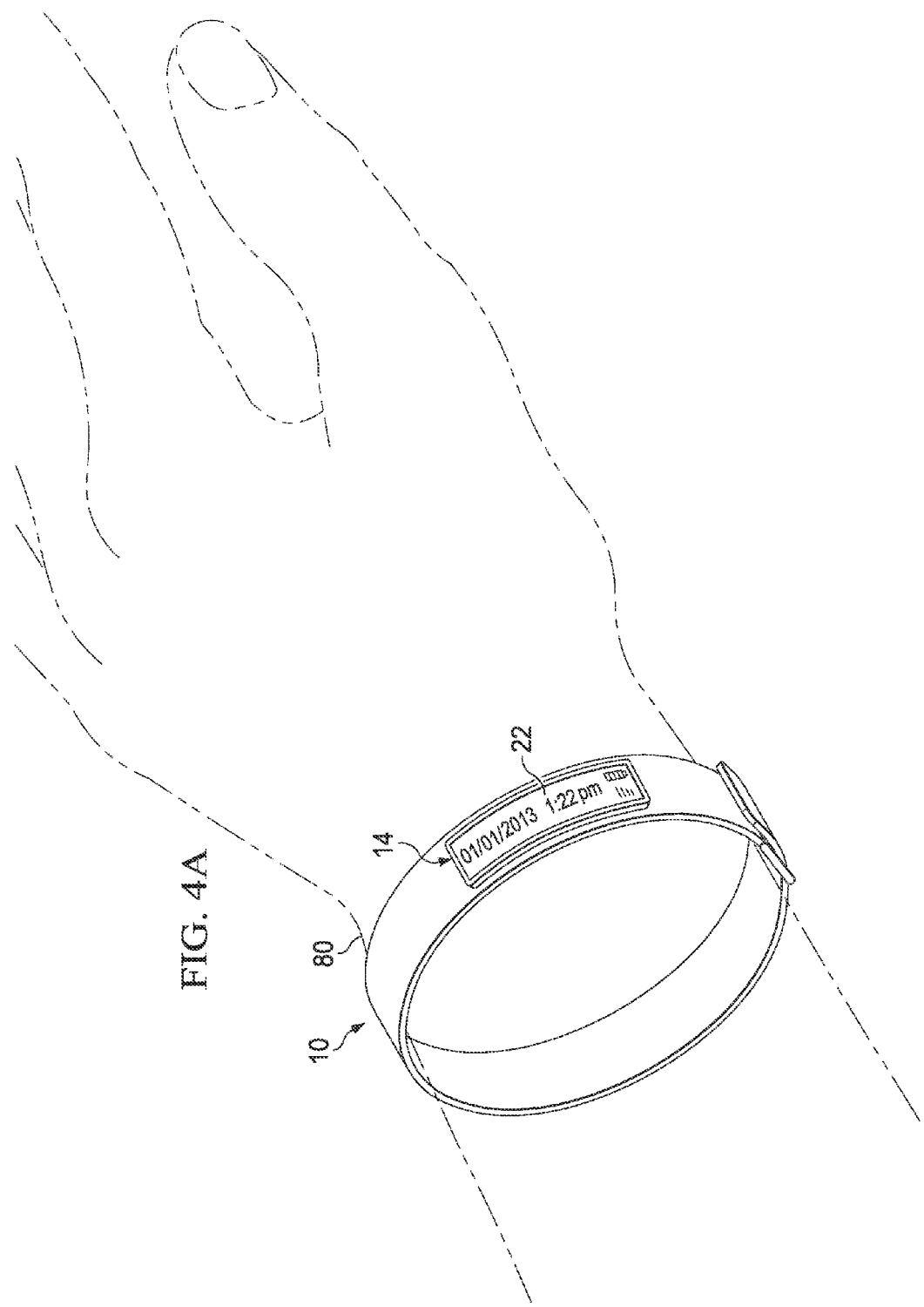

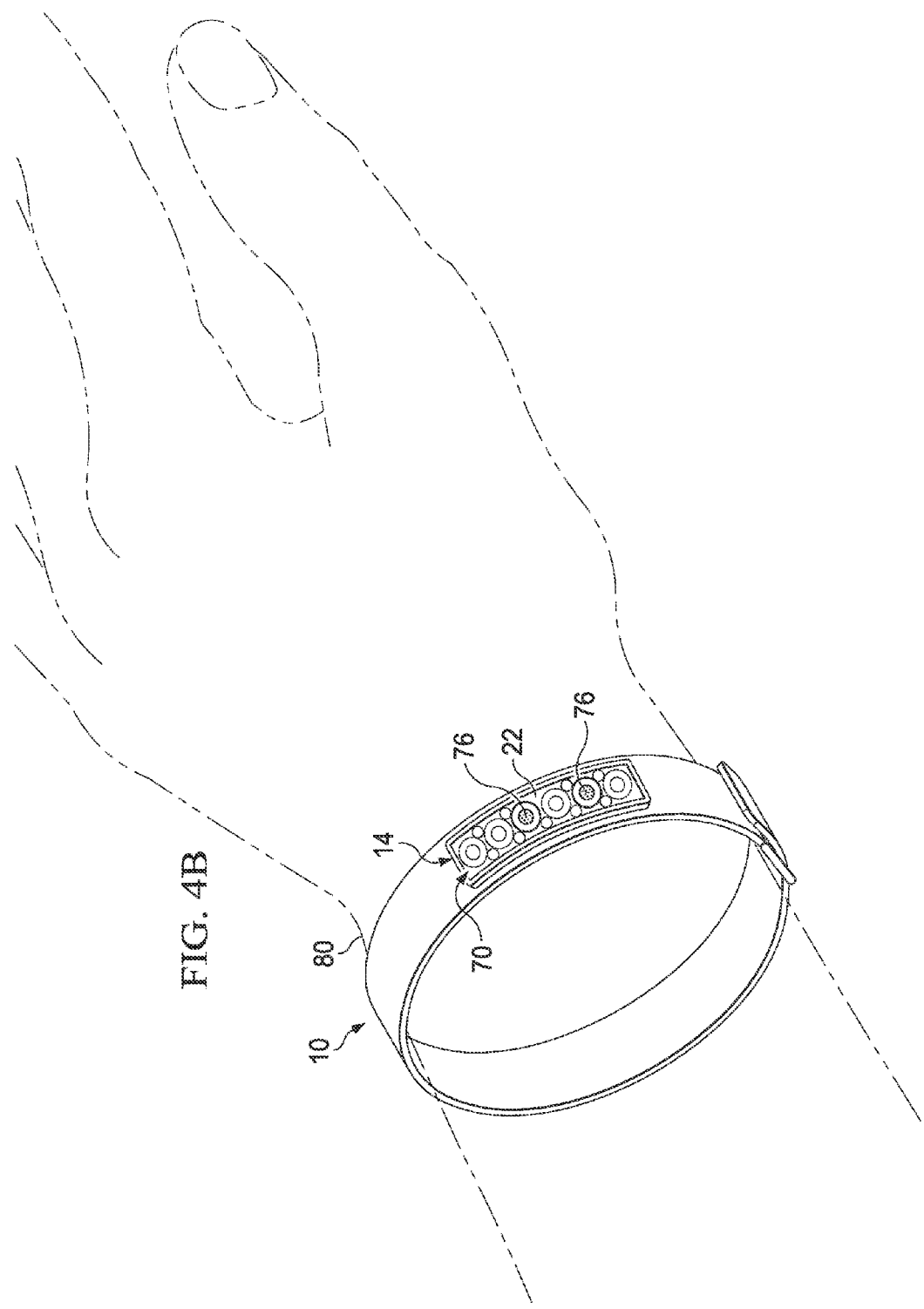

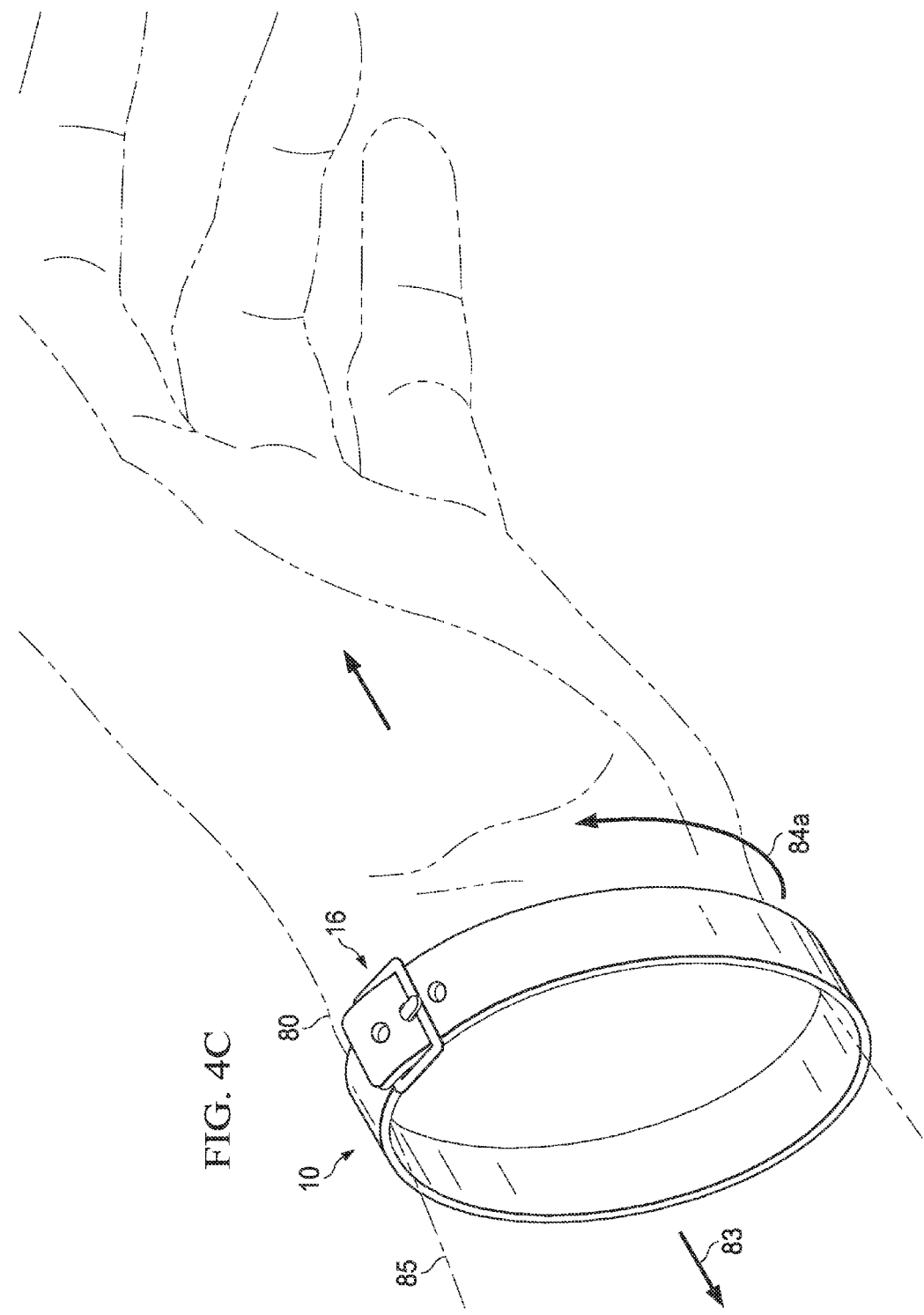

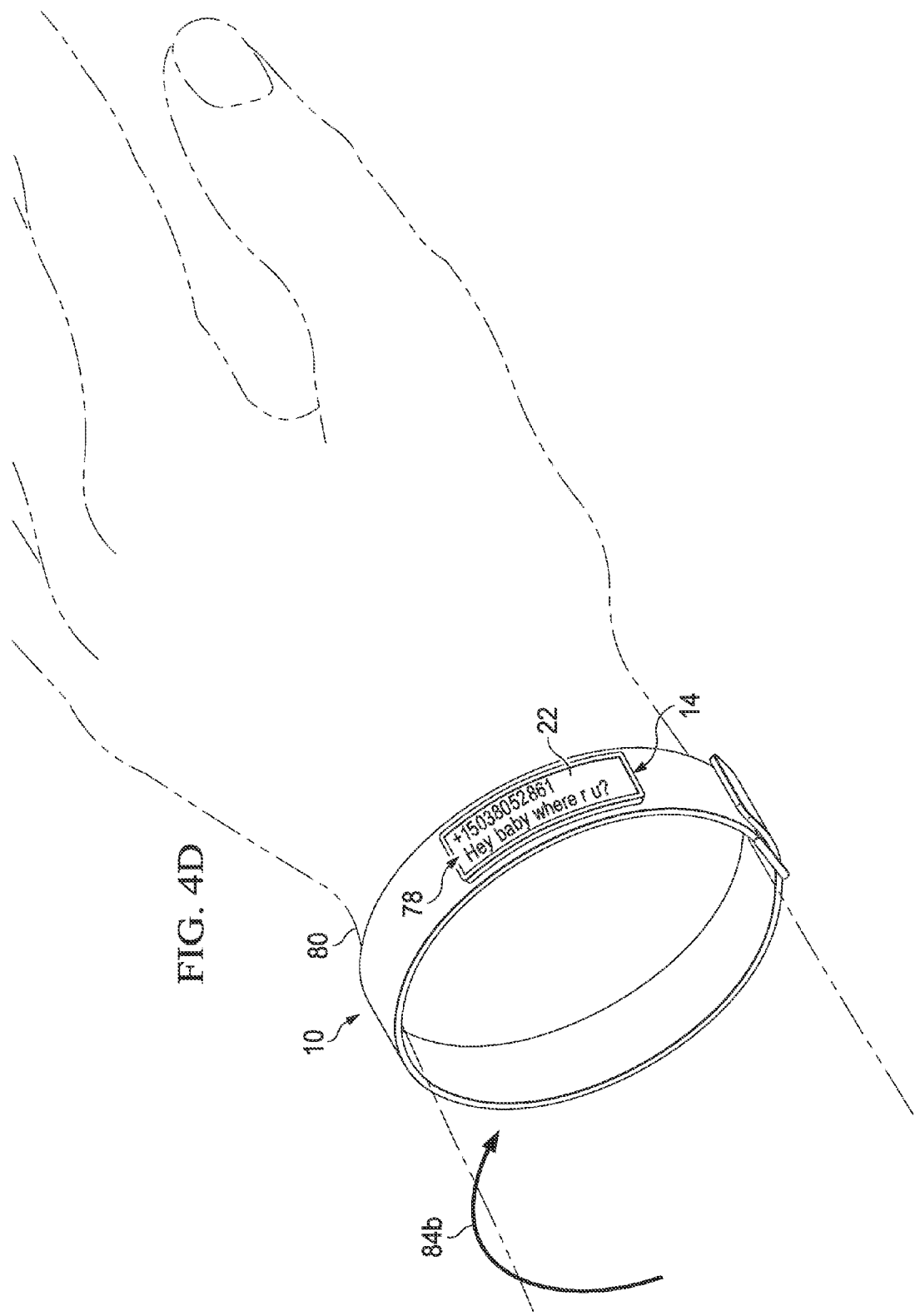

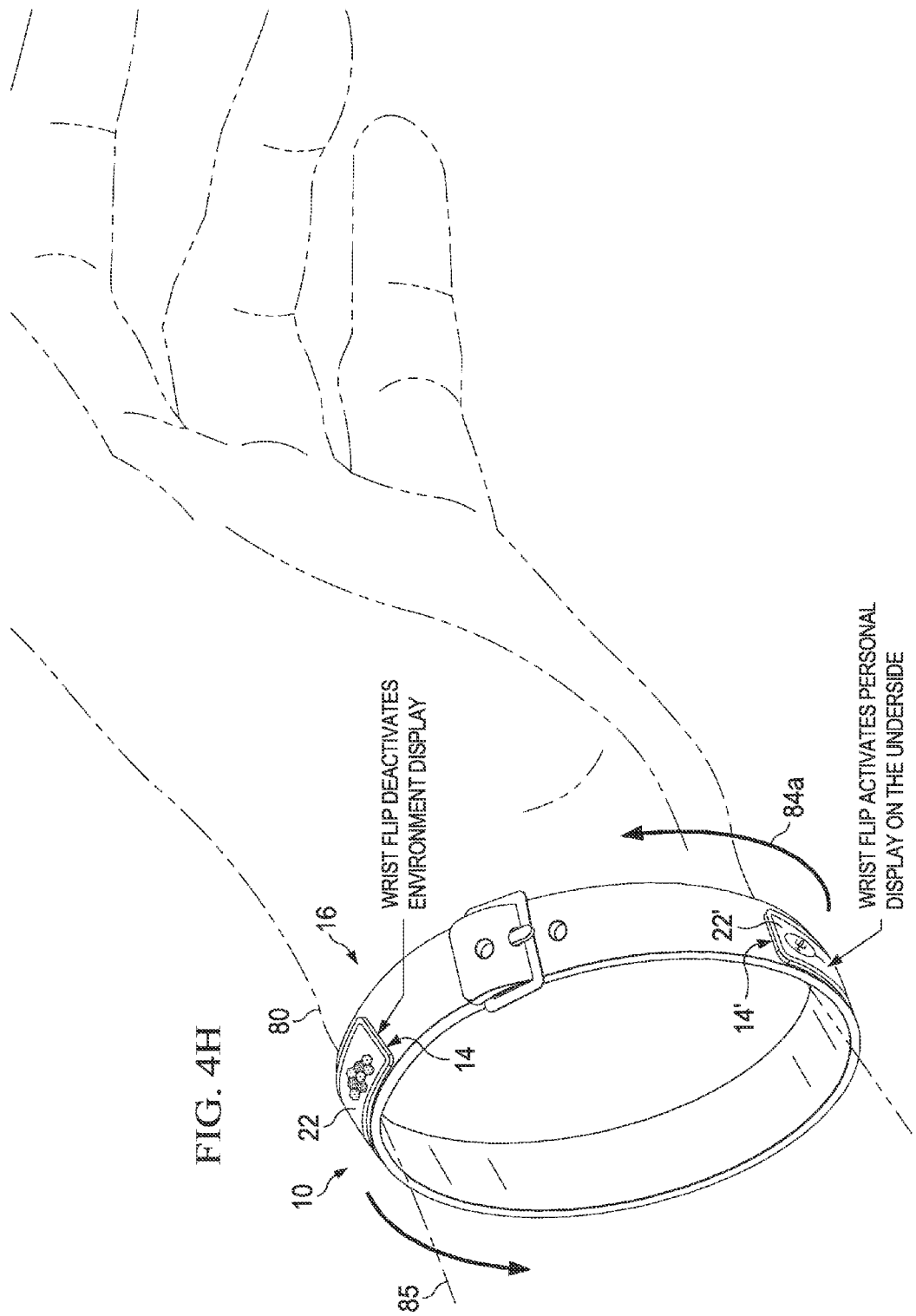

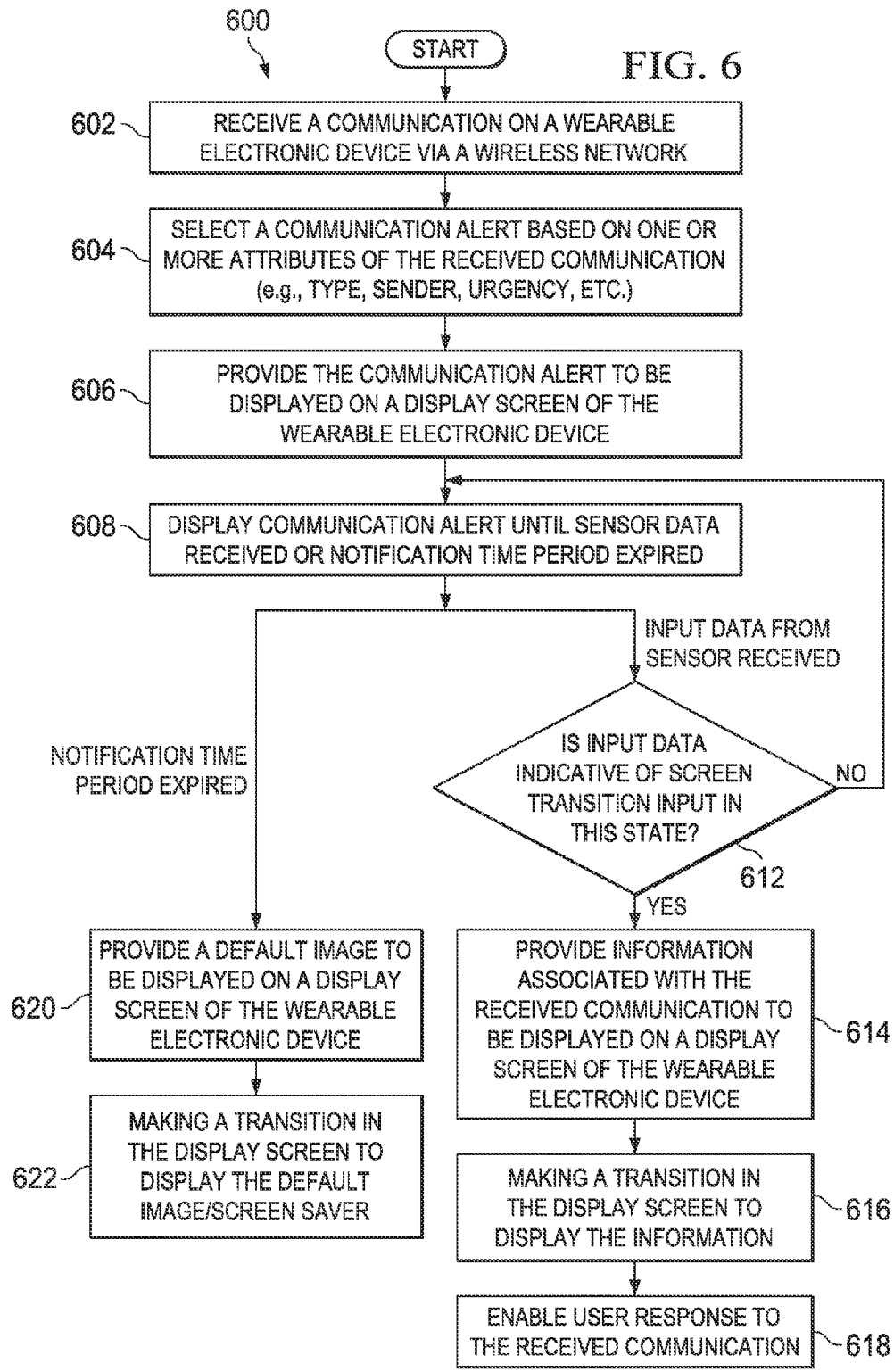

WEARABLE ELECTRONIC DEVICE HAVING HETEROGENEOUS DISPLAY SCREENS

TECHNICAL FIELD

Embodiments described herein generally relate to a wearable electronic device having heterogeneous display screens.

BACKGROUND

People have become increasingly attached to mobile electronic devices and in particular, to their mobile phones. People can be seen carrying and interacting with their mobile phones (and other mobile devices) during almost every aspect of their lives, including business, social, and personal times. Having constant access to communication from other people and services via a mobile phone is becoming entrenched as a societal norm. Although mobile phone interactions are generally accepted by others, they can be problematic in certain settings (e.g., business meetings, dinners, physical activities, classroom lectures, etc.). Moreover, many mobile phones have grown size, at least in part due to enhanced features and functionality. Consequently, the ability to discreetly view and respond to incoming communications on a mobile phone and other, even larger mobile devices, can be difficult. Hence, there is a desire to improve the ability of users to stay constantly connected, without necessarily interrupting or impeding the user's life when discretion and selectivity of received communications is preferred.

BRIEF DESCRIPTION OF THE DRAWINGS

To provide a more complete understanding of the present disclosure and features and advantages thereof, reference is made to the following description, taken in conjunction with the accompanying figures, where like references indicate like elements, in which:

FIG. 4A is a simplified orthographic view illustrating an example wearable electronic device, according to an embodiment of the present disclosure;

FIG. 4B is a simplified orthographic view illustrating an example wearable electronic device, according to an embodiment of the present disclosure;

FIG. 4C is a simplified orthographic view illustrating an example wearable electronic device, according to an embodiment of the present disclosure;

FIG. 4D is a simplified orthographic view illustrating an example wearable electronic device, according to an embodiment of the present disclosure;

FIG. 4H is a simplified orthographic view illustrating an example wearable electronic device with dual display screens, according to an embodiment of the present disclosure;

FIG. 4I is a simplified orthographic view illustrating an example wearable electronic device with dual display screens, according to an embodiment of the present disclosure;

FIG. 6 is a simplified flow diagram illustrating potential operations associated with an embodiment of the present disclosure;

The FIGURES of the drawings are not necessarily drawn to scale, as their dimensions can be varied considerably without departing from the scope of the present disclosure.

DETAILED DESCRIPTION OF EMBODIMENTS

The following detailed description sets forth embodiments of apparatuses, methods, and systems relating to wrist displays for a wearable electronic device. Features such as structure(s), function(s), and/or characteristic(s), for example, are described with reference to certain embodiments as a matter of convenience; various embodiments may be implemented with any suitable one or more of the described features.

Figure 1A:
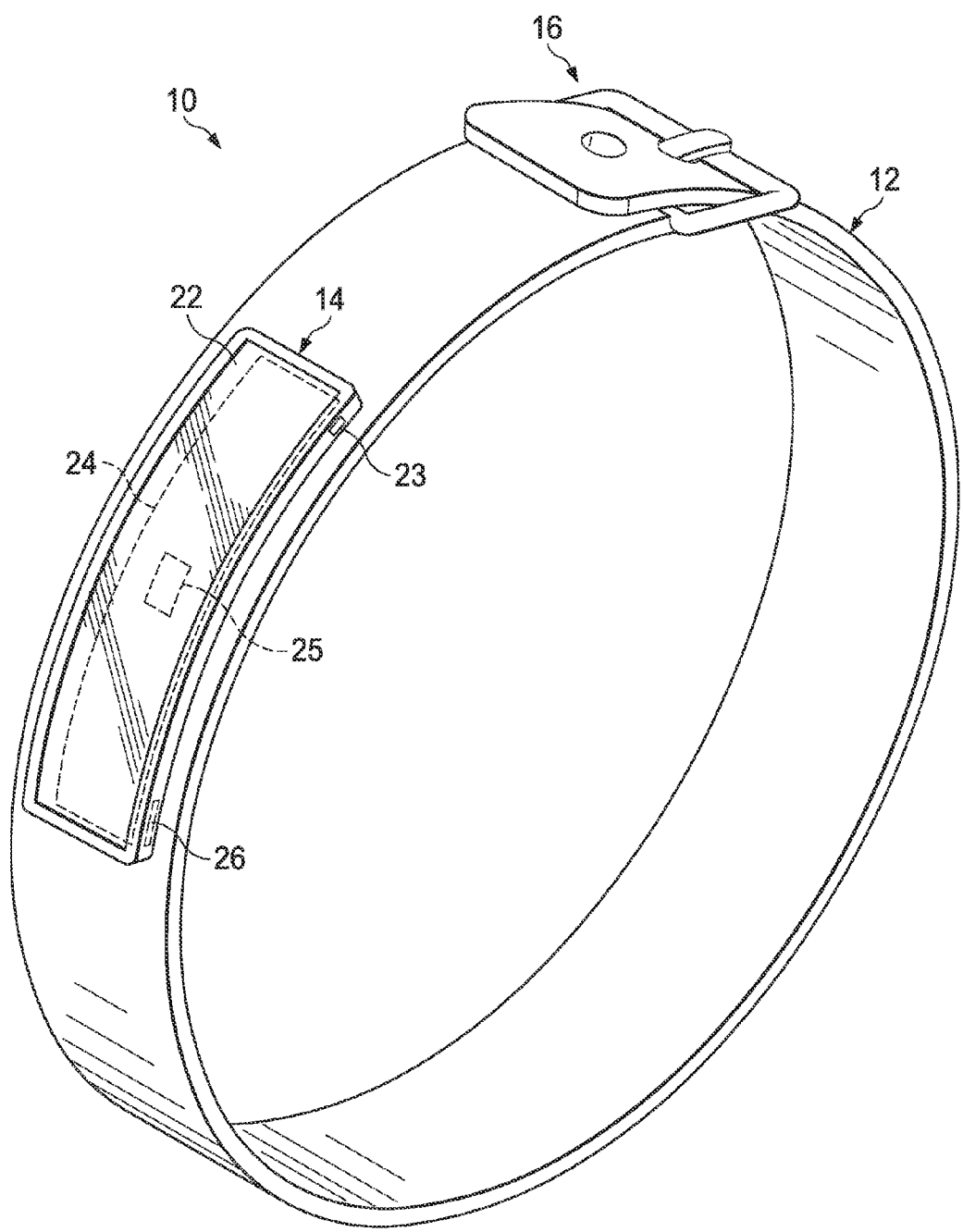
FIG. 1A is a simplified orthographic view illustrating an example wearable electronic device, according to an embodiment of the present disclosure.

FIG. 1A is a simplified orthographic view illustrating an embodiment of a wearable electronic device 10 according to an embodiment in the present disclosure. Wearable electronic device 10 may include a strap portion 12, a display portion 14 and a latch portion 16. Display portion 14 can include a display screen 22 and possibly, a biometric sensor such as a fingerprint sensor 24. Strap portion 12 may include a first end and a second end that may be coupled together using latch portion 16 to secure the wearable electronic device to a user (e.g., around a wrist, arm, etc. of the user). In at least one embodiment, an input device, such as a motion sensor 25 for example, can be provided on wearable electronic device 10 for detecting user input, for example, in the form of movement. In one or more embodiments, display portion 14 can include a port 26 to facilitate charging a battery or capacitor, communication and/or control of wearable electronic device 10. Display portion 14 may also include a button 23 to enable certain functions on wearable electronic device 10 to occur in response to a button press.

For purposes of illustrating certain example features and uses of wearable electronic device 10, it is important to understand the communications that may be traversing the network environment and the scenarios in which the device may be particularly beneficial. The following foundational information may be viewed as a basis from which the present disclosure may be properly explained.

Today, personal mobile electronic devices (also referred to herein as 'mobile devices') are present in virtually every facet of life. In particular, mobile phones are often carried by users throughout the day and night. This allows the users to receive, respond to, and initiate communications (e.g., phone calls, text messages, emails, social media communications, etc.) via their mobile phones at any time. While this capability can often be convenient and useful, in many instances, the use of a mobile phone can be disruptive, annoying, and rude to others.

Mobile phones and other smaller electronic devices are often carried in purses, pants pockets, shirt pockets, or in a clip attached to a belt. These mobile devices typically provide some sort of notification signal, such as an audio signal, a vibration signal, or both, to alert the user of an incoming communication. Responding to such notification signals generally requires the user to retrieve the mobile phone, read a display and interact with the device in an appropriate way (e.g., via a touch screen, via a manual button, etc.).

These activities can be disruptive in numerous situations (e.g., business meetings, dinners, lectures, movies, performances, workouts, religious ceremonies, etc.) In fact, many establishments and organizations require users to power down their mobile phones or use a 'Silent' option to minimize disruptive noises and distractions. Even the 'Silent' option, however, can prove disruptive. Once a vibration is detected, a user typically has to retrieve the mobile phone (e.g., from a purse, pocket, clip, etc.) and interact with the device using their hands. Furthermore, vibrations of a 'Silent' option are often loud enough to be heard by others nearby. Nevertheless, the demand by users for continuous access to notifications from their mobile phones persists. Moreover, in some instances, the need for continuous access to notifications can be necessary. For example, a user may need to have continuous access to notifications from a healthcare provider of an ill spouse or other relative. In another example, a spouse may want to have continuous access to communications from his spouse (e.g., waiting for the birth of a child), a childcare provider, etc.

In some scenarios, users may inadvertently not carry their mobile devices with them or may not have a good option for carrying the mobile device in the particular scenario. For example, a user could accidentally leave their home or office without their mobile phone, a user could leave their phone in another room or office beyond the user's hearing range, a battery of the mobile phone could die, a user may choose to not take their mobile phone during an exercise workout or other outing, a user could temporarily misplace, lose, or break their mobile phone, etc. In these and other instances, not having access to their mobile phone could cause anxiety and stress for the user. In addition, in these and other similar scenarios, the user may be unable to receive or send communications in real-time.

Another problem for users who check incoming communications on their mobile phones (or other devices) in public or semi-public settings, involves the inability to maintain discretion. Mobile phones, and many other mobile devices, are often large enough to be easily read by another person in close proximity. Accordingly, accessing an incoming text message on a subway, may result in one or more adjacent subway riders reading the name or phone number of the message sender and possibly the text message itself.

Wearable electronic device 10 as shown and described herein, overcomes many of these problems and provides a solution for users who desire continuous access to mobile device communications, without the obtrusive and sometimes inconvenient nature of a typical mobile phone or other handheld mobile device. Particular embodiments described herein provide for a wearable electronic device, such as a bracelet, watch, wristband, armband, or other wearable device that includes a circuit board coupled to a plurality of electronic components (which includes any type of components, elements, circuitry, etc.). Wearable electronic device 10 is configured to receive communications that are also received on the user's handheld mobile device (e.g., text messages, emails, etc.) and from other selected services (e.g., social media, etc.). (or information about the communications) Wearable electronic device 10 can be attached to a user (e.g., the user's wrist), such that the user can easily access it at all times. Thus, the user can avoid cumbersome manipulations of a handheld mobile device by retrieving it from an article of clothing or a purse, bag, etc. The user can also avoid missed calls and other missed communications when a handheld mobile device has been left somewhere (e.g., in another room of a house, in a bathroom, at home when the user is at work, in an office when the user walks down the hall, etc.).

Wearable electronic device 10 can also protect the privacy of received communications and provide unobtrusive, yet visually attractive communication alerts. In at least one embodiment, a communication alert is a graphic design that can be displayed on display screen 22 to alert a user that wearable electronic device 10 received a communication. The graphic design can maintain the privacy of the communication by not displaying personal, human-readable information related to the communication. Thus, textual information such as names, email addresses, phone numbers, message content, etc. may not be provided in the graphic design. In at least one embodiment, the graphic design is artistic, aesthetically pleasing, and possibly color oriented. An arbitrary notification pattern may be provided in the graphic design to indicate a type of communication that was received (e.g., email, text, phone call, social media, etc.). The meaning of the arbitrary notification pattern can be known and recognized by the user but not necessarily by others. In at least some embodiments, a notification pattern can also indicate a level of significance or importance of the sender and/or a level of urgency of the communication itself.

The user can choose to ignore or receive the communication. In one example, ignoring the communication alert can result in the continued display of the communication alert for a pre-configured notification time period, without displaying any human-readable information associated with the communication. Alternatively, the user may choose to receive the communication by providing appropriate detectable input (e.g., twist wrist, touch screen, speak, etc.). If the user chooses to receive the communication, then the graphic design in display screen 22 can be transitioned to data oriented, human-readable information associated with the communication. In addition, one or more options may be provided to enable the user to respond to the communication. The user may also perform other actions such as saving or deleting the communication information.

Turning to the particular features of at least one embodiment of wearable electronic device 10, shown in FIG. 1A, wearable electronic device 10 includes strap portion 12, which can be made using numerous materials and designs. Strap portion 12 may be made of one or more materials including metal and metal alloys (e.g., stainless steel, aluminum, tin, iron, gold, silver, platinum, titanium, etc.), natural fabrics, synthetic fabrics, fibers and blends thereof (e.g., cotton, polyester, nylon, satin, silk, wool, leather, etc.), synthetic polymers (plastic, rubber, elastic, carbon fiber, injection molding), combinations thereof or the like. In one or more embodiments, strap portion 12 may be of a solid unibody construction (as shown in FIG. 1A) or may include links, chains, cables, weaves, combinations thereof or the like. In some embodiments, wearable electronic device 10 can include a strap that is formed as a solid strap without a latch portion. The ornamental design and material construction of strap portion 12 can be adjusted in any manner to suit any designer, manufacturer and/or vendor without departing from the scope of the embodiments described in the present disclosure.

Display portion 14 may be coupled to (e.g., disposed within/on and/or supported by) strap portion 12. Display screen 22 may be coupled to display portion 14. In one or more embodiments, display screen 22 is a surface on which images and data can be displayed including a liquid crystal display (LCD) screen, transparent LCD screen, light-emitting diode (LED) display screen, transparent LED display screen, organic light-emitting diode (OLED) display screen, transparent LED display screen or any other suitable display screen system. Display screen 22 may also be a touch screen display, which may include a capacitive or resistive touch screen layer over the screen of display screen 22.

In at least one embodiment, a second display portion with a second display screen may be provided in wearable electronic device. The second display screen could be configured as the same type of display screen as display screen 22, or could be configured as a different type of display screen. Moreover the second display screen may be provided anywhere in wearable electronic device 10. For example, the second display screen could be adjacent to display screen 22, or could be separated by any amount, depending on particular needs and implementation requirements. Any of the embodiments described herein could be implemented in conjunction with single display screen 22, a second display screen, or a combination thereof.

In at least one embodiment, motion sensor 25 can be provided on wearable electronic device 10 for detecting movement of wearable electronic device 10, which may be caused by a user's wrist to which it is secured. In an example implementation, motion sensor 25 can include an accelerometer and a gyroscope. An accelerometer is an electromechanical device that can measure the linear acceleration of wearable electronic device 10, which can be caused by moving the wrist. The accelerometer can also be used to sense the orientation of wearable electronic device 10 relative to the earth's surface. A gyroscope is a device used for measuring the orientation of the device directly. When measurements from the accelerometer and the gyroscope are combined, wearable electronic device 10 can be configured with logic to identify a particular movement. The particular movement could be forwards and backwards, up and down, left and right, rotational movements (i.e., pitch, roll, and yaw), or any suitable combination thereof.

Wearable electronic device 10 can be configured with logic to determine whether particular input data from motion sensor 25 is indicative of a movement that represents screen transition input during the current state. The term 'screen transition input' as used herein, is intended to mean input from a user (or possibly another device) that represents a command to wearable electronic device 10 to transition a current display in a display screen to another display in the same display screen or a different display screen. A 'display' in a display screen is intended to mean any information, data, graphics, images, animations, pictures, etc. that is shown in the display screen. Input from a user (or device) that is detected and recognized as a transition command may vary depending on a state of wearable electronic device 10, and the particular type of sensor (e.g., motion, touch, audio, button press, etc.) configured to detect input during the state.

In at least one embodiment of wearable electronic device 10 configured with motion sensor 25, a particular movement can represent screen transition input during a particular state, such as when a communication alert is being displayed on display screen 22. The particular movement could be, but is not limited to, a partial rotation of the wearable electronic device 10 when a user twists his wrist forward and backward, shaking when the user shakes the device, or any other movement or combination of movements detectable and measurable by motion sensor 25. Thus, when a user receives a communication alert and wants to see information associated with the received communication, in one or more embodiments the user can cause a particular movement of wearable electronic device, such as twisting his wrist forward, and then back again. This movement can be detected and identified as screen transition input provided by the user to effect a transition from the display of the communication alert to a display of information associated with the received communication.

In one or more embodiments, display portion 14 may also (or alternatively) include a biometric sensor such as a fingerprint sensor in display screen 22. A biometric sensor may be provided for sensing particular biological characteristics of a human user. As used herein, 'sensing' is intended to mean detecting, scanning, measuring, and/or recognizing the particular biological characteristics being sensed. Biometric technology can be used to sense and analyze human body characteristics such as, but not limited to, voice patterns, speech, fingerprints, eye retinas and/or irises, facial features, hand features, palm prints, pulse features, and vein patterns. A biometric sensor can be configured to sense a particular biometric characteristic of a user. For example, a fingerprint sensor can be used to sense a fingerprint, a microphone can be used to sense a voice (for both voice identification and speech recognition), an eye sensor can be used to sense eye retinas and/or irises, a facial sensor can be used to sense facial features, a hand sensor can be used to sense hand measurements/geometry and/or palm prints, a pulse sensor can be used to sense pulse features, and a vein pattern sensor can be used to sense vein patterns.

In particular, a fingerprint sensor may be configured to capture one or more fingerprints at a plurality of locations and a plurality of orientations. The fingerprint sensor may be an optical fingerprint sensor or a capacitive fingerprint sensor configured to capture one or more fingerprint images of one or more fingers of a user that may be placed on display screen 22. As configured in conjunction with an optical fingerprint sensor, display screen 22 may be transparent (e.g., transparent OLED, transparent LED, etc.) and the fingerprint sensor may be configured below display screen 22. As configured in conjunction with a capacitive fingerprint sensor, display screen 22 may be of any configuration (e.g., transparent or not transparent) and the fingerprint sensor may be configured above display screen 22. In some embodiments, a capacitive fingerprint sensor and capacitive touch screen may be configured together as a single multi-function touch screen.

In general terms, optical fingerprint sensors project a light onto a finger using one or more light emitting elements and capture light reflected from the finger using a charge coupled devices (CCD). The captured light represents a fingerprint image of the fingerprint (e.g., ridges and valleys of the fingerprint). The captured light can be converted into a digital representation of the fingerprint image using an analog to digital converter (ADC) or other like device. Capacitive fingerprint sensors can measure changes in capacitance between ridges and valleys of a fingerprint that can be converted into corresponding data values representing the ridges/valleys of the fingerprint; thus, creating a digitized image of the fingerprint. A digitized fingerprint image of a user's fingerprint can be processed (e.g., using processors, logic, etc.) to determine identification information associated with the user, which may be used to identify the user.

Wearable electronic device 10 can be configured with logic to determine whether particular input data from fingerprint sensor 25 is indicative of a fingerprint that represents screen transition input during the current state. In at least one embodiment of wearable electronic device 10 configured with fingerprint sensor 24, a fingerprint can represent screen transition input during a particular state, such as when a communication alert is being displayed on display screen 22. In at least one embodiment, any fingerprint can represent screen transition input and logic of wearable electronic device 10 can identify any digitized fingerprint as screen transition input. In other embodiments, only certain fingerprints (e.g., determined to belong to an authorized user) represent screen transition input.

In at least one embodiment, display screen 22 of wearable electronic device 10 is a touch screen. Wearable electronic device 10 can be configured with logic to determine whether particular input data from the touch screen is indicative of a touch that represents screen transition input in the current state. In at least one embodiment of wearable electronic device 10 configured with a touch screen, a particular touch can represent screen transition input during a particular state, such as when a communication alert is being displayed on display screen 22. The particular touch could be a single finger or multi-finger touch including, for example, a tap, a double tap, a swipe, a touch and hold, or any other touch or combination of touches detectable by the touch screen.

Although embodiments of wearable electronic device 10 could be configured such that a particular motion, fingerprint and/or touch represents a screen transition input, other types of gestures, signals, biometric input, etc. representing screen transition input are also within the broad scope of the present application. For example, voice commands or other audio input, may be received by a microphone in wearable electronic device 10, and may be identified as screen transition input during the current state. In yet another example, a button press signal may be received when a physical button (e.g., button 23) is pressed by a user. The button press signal may be identified as a screen transition input during a current state. In yet another example, user gestures may be detected by a gesture recognition sensor and identified as a screen transition input during the current state. In addition to fingerprints, other biometric characteristics (e.g., voice patterns, eye retinas and/or irises, facial features, hand features, palm prints, pulse features, vein patterns, etc.) may be detected by an appropriate biometric sensor and identified as a screen transition input during the current state. These audio input, button press signals, biometric input, and gestures may be interpreted using one or more processors, logic, software, etc. These example embodiments are only a few of the many other methods or means that can be used to enable screen transition input during a particular state. Virtually any other methods or means may be used to enable screen transition input during a particular state and thus, are clearly within the scope of the present disclosure.

Display portion 14 and display screen 22 may be formed of flexible materials that may allow each to bend and flex in conjunction with the strap portion 12 when wearable electronic device 10 is worn by a user. Display portion 14 can be a rectangular shape (as shown in FIG. 1A), an elliptical shape or any other shape as determined by a designer or manufacturer. Display portion 14 and display screen 22 may be sufficiently large to accommodate multiple fingers of a user that may be placed on display screen 22. If display portion 14 includes a fingerprint sensor, the fingerprint sensor may be configured beneath display screen 22 to scan the one or more fingers at any location and any orientation (e.g., direction of a finger) on display screen 22.

Latch portion 16 may be located at a first end of the strap portion 12 and may facilitate coupling (e.g., fastening, locking, connecting, etc.) the first end to the second end in order to secure the wearable electronic device 10 to a user (e.g., wrist, arm, etc.). In one example, latch portion 16 can include a buckle with a frame, a bar, a chape and a prong attached to one end of strap portion 12. The other end of strap portion 12 can be configured with multiple holes for adjustably securing the ends of strap portion 12 to each other by receiving the prong into a selected one of the holes when the other end of strap portion 12 is inserted through the frame, around the bar, and back through the frame. Thus, latch portion 16 enables wearable electronic device 10 to be secured to a user's wrist.

In other embodiments, any latch portion having a suitable latch mechanism configured to secure opposite ends of strap portion 12 together, can be used with strap 12 of wearable electronic device 10. A mating portion can be configured on one end of strap portion 12 to include one or more mating elements to facilitate coupling with the latch mechanism on the other end of strap portion 12 in order to secure the ends of strap portion 12 together. For example, suitable latch mechanisms could include pin-type latch mechanisms, pressure-type latch mechanisms, magnetic-type latch mechanisms, hook-type latch mechanisms, ratchet-type latch mechanisms, combinations thereof, or the like. In one or more embodiments, latch portion 16, and alternative embodiments of the latch portion, may be made of one or more materials including metal and metal alloys (e.g., stainless steel, aluminum, tin, iron, gold, silver, platinum, titanium, etc.), polymers (plastic, rubber, elastic, carbon fiber, injection molding), combinations thereof or the like.

In one or more embodiments, display portion 14 can include port 26 to facilitate charging a battery or capacitor, communication and/or control of the wearable electronic device 10. For example, electrical current and signals can be passed through a plug-in connector (e.g., whose male side protrusion connects to port 26 and whose female side connects to a power device or another electronic device or vice-versa) or a wireless connector (e.g., WiFi, Bluetooth™, etc.) to recharge an on-board battery or capacitor and/or provide a communication path to electronics in wearable electronic device 10. Note that any number of connectors (e.g., Universal Serial Bus (USB) connectors (e.g., in compliance with the USB 3.0 Specification released in November 2008), Thunderbolt™ connectors, a non-standard connection point such as a docking connector, etc.) can be provisioned in conjunction with electronic device 10. Thunderbolt™ and the Thunderbolt logo are trademarks of Intel Corporation in the U.S. and/or other countries. Virtually any other electrical connection means and methods could be used and, thus, are clearly within the scope of the present disclosure. Port 26 may be configured on any side of display portion 14.

In one or more embodiments, display portion 14 includes button 23 to allow a user to manually initiate interaction with wearable electronic device 10. Button 23 may trigger signals indicative of screen transition input to override other images currently being displayed in display screen 22 of display portion 14. A user interface may be displayed in display screen 22 of display portion 14, and may be configured to allow user to interact with wearable electronic device 10 via a touch screen, voice signals, etc.

In one or more embodiments, wearable electronic device 10 can include a wireless communication circuitry (e.g., Wi-Fi module, Bluetooth™ module, near field communication (NFC) module, or other wireless communication circuitry) to allow wearable electronic device 10 to communicate with one or more other electronic devices or a network through a wireless connection. The wireless communications may be inclusive of wireless technologies (e.g., Institute of Electrical and Electronics Engineers (IEEE) Std 802.11™-2012, published Mar. 29, 2012, IEEE Std 802.16™-2012, published Aug. 17, 2012, WiFi, WiMax, Dedicated short Range Communications (DSRC), etc.), satellite, cellular technologies (e.g., 3G/4G/5G/nG, etc.), other radio frequencies (e.g., near field communications (NFC), radio frequency identification (RFID), etc.), and/or any other networking protocols that facilitate wireless communications in a network environment. In an embodiment, a plurality of antennas can be provisioned in conjunction with wearable electronic device 10, which may be associated with wireless connection activities. Additionally, wearable electronic device 10 can also include wireless communication circuitry to facilitate wireless charging of a battery or capacitor (e.g., wireless Qi inductive electrical power transfer standard).

Figure 1B:
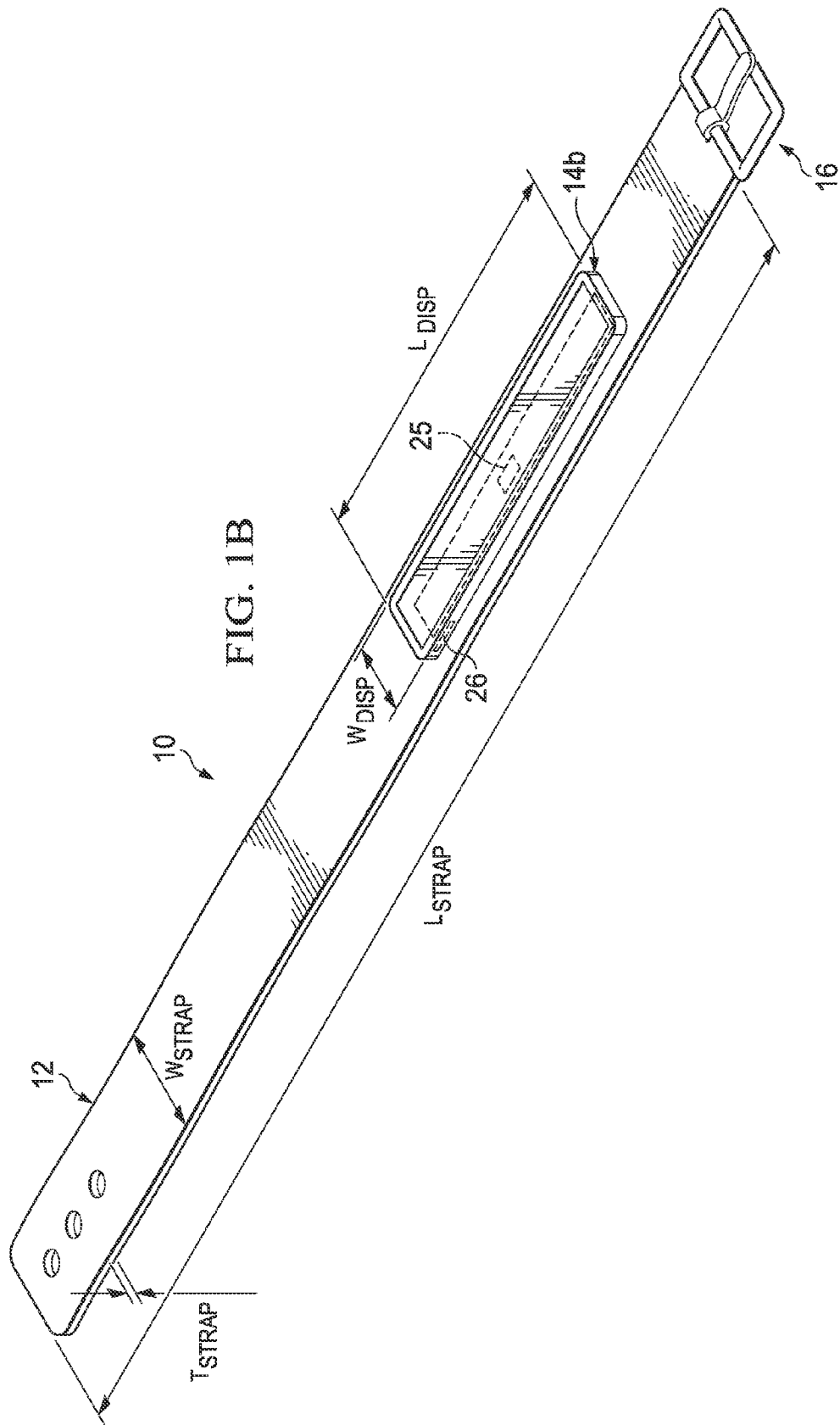
FIG. 1B is a simplified orthographic view illustrating an example wearable electronic device, according to an embodiment of the present disclosure.

Turning to FIG. 1B, FIG. 1B is a simplified orthographic view illustrating an embodiment of wearable electronic device 10 in accordance with one embodiment of the present disclosure. In FIG. 1B, wearable electronic device 10 is illustrated in an unsecured configuration to simplify the description of various features. As shown in FIG. 1B, strap portion 12 may have a length $L_{STRAP}$, which may range from approximately 5 inches to approximately 10 inches. Strap portion 12 may have a width $W_{STRAP}$, which may range from approximately 8 mm to approximately 65 mm. Strap portion 12 may have a thickness $T_{STRAP}$, which may range from approximately 3 mm to approximately 40 mm. In more general terms, strap portion 12 can be constructed having varying overall lengths to accommodate securing wearable electronic device 10 to a variety of different users, which may have a range of different body proportions, etc. and/or a variety of different user body parts (e.g., wrists, arms, ankles, etc.) which may have a range of different corresponding sizes. The ornamental design and material construction of strap portion 12 can be adjusted in any manner to suit any designer, manufacturer and/or vendor without departing from the scope of the embodiments described in the present disclosure.

Although display portion 14 is illustrated as extending above a top surface of strap portion 12, it should be understood that display portion 14 may also be flush or approximately flush with the top surface of strap portion 12. In at least one embodiment, display portion 14, display screen 22, and fingerprint sensor 24 may be sufficiently large to accommodate multiple fingers of a user that may be placed on display screen 22. Display portion 14 may have a width $W_{DISP}$, which may range from approximately ⅓ of the width $W_{STRAP}$ to approximately equal to the width $W_{STRAP}$. Display portion may have a length $L_{DISP}$, which may range from approximately 1/10 of the length $L_{STRAP}$ to approximately 9/10 of the length $L_{STRAP}$, or a length that does not result in display portion overlapping when the latch mechanism is secured around a user's wrist.

In one or more embodiments, wearable electronic device 10 is an electronic bracelet, watch, wristband or armband. In still other embodiments, wearable electronic device 10 may be any suitable electronic device having a display such as a mobile device, a tablet computer and/or a tablet device (e.g., i-Pad™), Phablet™, a personal digital assistant (PDA), a smartphone, an audio system, a movie player of any type, or any other device, component, element, or object capable of voice, audio, video, media, or data exchanges in a network and having a display screen. In one or more embodiments, electronic elements (e.g., processors, controllers, memory, etc.) for wearable electronic device 10 may reside in display portion 14, in strap portion 12, latch portion 16, or in any suitable combination thereof.

In at least one example embodiment, the circuit board of wearable electronic device 10 may be a general circuit board that can hold various components of an internal electronic system of wearable electronic device 10. The components may include a central processing unit (CPU), a memory, etc. The circuit board can also couple to one or more connectors in order to accommodate other peripherals sought to be used by a user of wearable electronic device 10. More specifically, the circuit board can provide the electrical connections by which the other components of the system can communicate.

Any processors (inclusive of digital signal processors, microprocessors, supporting chipsets, etc.), memory elements, etc. can be suitably coupled to the circuit board based on particular configuration needs, processing demands, computer designs, etc. Note that particular embodiments of the present disclosure may readily include a System on a Chip (SOC) central processing unit (CPU) package. An SOC represents an integrated circuit (IC) that integrates components of a computer or other electronic system into a single chip. The chip may contain digital, analog, mixed-signal, and often radio frequency functions: all of which may be provided on a single chip substrate.

Additionally, embodiments of the present disclosure may include logic to achieve or foster the screen display and transition activities related to incoming communications as outlined herein. Note that logic could be implemented in a variety of manners. For example, logic could be implemented in software, firmware, hardware, or any suitable combination thereof.

Figure 2:
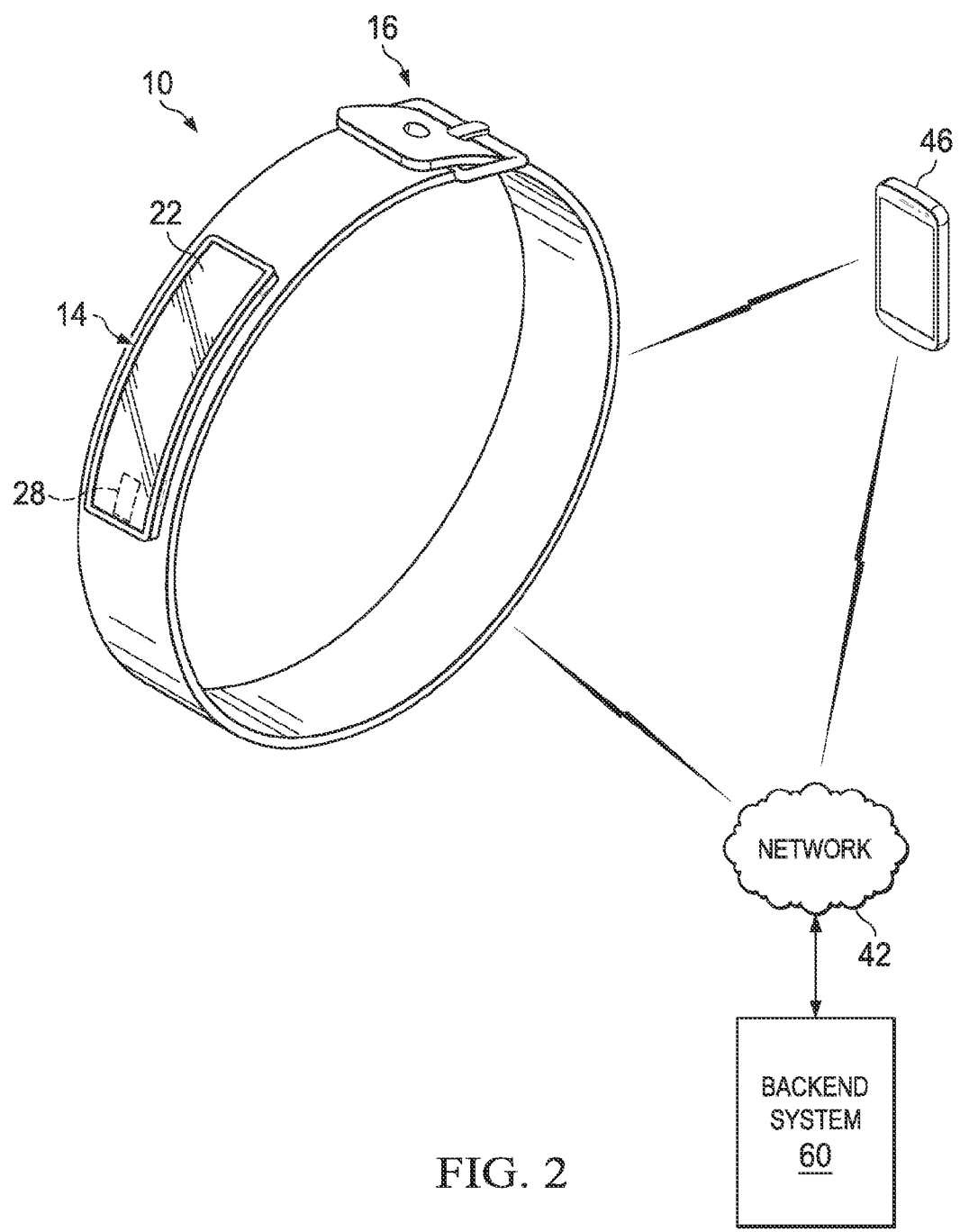
FIG. 2 is a simplified block diagram illustrating a simplified orthographic view of a wearable electronic device in an example network environment according to an embodiment of the present disclosure.

Turning to FIG. 2, FIG. 2 is a simplified block diagram illustrating an embodiment of wearable electronic device 10 in accordance with one embodiment of the present disclosure. Wearable electronic device 10 has its ends coupled together in the configuration shown in FIG. 2. Wearable electronic device 10 can include display portion 14, which can include a wireless module 28. Wireless module 28 (e.g., cellular, module, Wi-Fi module, Bluetooth™ module, WiDi module, or other wireless communication circuitry) may allow wearable electronic device 10 to communicate with a network 42, mobile device 46, and possibly other electronic devices through a wireless connection. Wearable electronic device 10 may communicate with a backend system 60 through network 42.

In an embodiment, the wireless connection may be a wireless personal area network (WPAN) to interconnect wearable electronic device 10 to network 42, mobile device 46, and possibly other electronic devices within a relatively small area (e.g., Bluetooth™, invisible infrared light, Wi-Fi, WiDi, etc.). In another embodiment, the wireless connection may be a wireless local area network (WLAN) that links wearable electronic device 10 to network 42, mobile device 46, and possibly other electronic devices over a relatively short distance using a wireless distribution method, usually providing a connection through an access point for Internet access. The use of spread-spectrum or OFDM technologies may allow wearable electronic device to move around within a local coverage area, and still remain connected to network 42, mobile device 46, and possibly other electronic devices. The wireless connection may also include any cellular wireless (e.g., 3G/4G/5G/nG, LTE, etc.), WiFi/ WiMax, satellite, or other similar connection to network 42. Such connections can facilitate communications with backend system 60.

Network 42 may be a series of points or nodes of interconnected communication paths for receiving and transmitting packets of information that propagate through network 42. Network 42 offers a communicative interface and may be any local area network (LAN), wireless local area network (WLAN), metropolitan area network (MAN), Intranet, Extranet, WAN (e.g., the Internet), virtual private network (VPN), or any other appropriate architecture or system that facilitates communications in a network environment. Network 42 may be inclusive of wire line technologies (e.g., Ethernet, T1 lines, etc.) and any wireless technologies previously discussed herein. Network 42 can comprise any number of hardware or software elements coupled to (and in communication with) each other through a communications medium.

Backend system 60 may include any one or more network elements configured to link a mobile phone and selected services (e.g., cloud-based services, services on mobile device 46 that can push alert, messages, and other communications to backend system, etc.) to a wearable electronic device. As used herein, the term 'network element' is meant to encompass servers, routers, switches, gateways, bridges, loadbalancers, firewalls, inline service nodes, proxies, processors, modules, or any other suitable device, component, element, proprietary appliance, or object operable to exchange information in a network environment. This network element may include any suitable hardware, software, components, modules, interfaces, or objects that facilitate the operations thereof. This may be inclusive of appropriate algorithms and communication protocols that allow for the effective exchange of data or information.

Mobile device 46 may be a smartphone, a cellphone, or any other computer (e.g., notebook computer, laptop, tablet computer or device), phablet, personal digital assistant (PDA), Google Android™, iPhone™, iPad™, Microsoft Surface™, Google Nexus™, multipurpose pocket computer, personal digital assistant (PDA), audio system, movie player, gaming device, etc. If mobile device has an assigned wireless (e.g., cellular, Wi-Fi, etc.) phone number for receiving phone calls and/or text messages, then wearable device 10 can receive those text messages and phone call notifications. This mobile phone may include any suitable hardware, software, components, modules, interfaces, or objects that facilitate the operations thereof. This may be inclusive of appropriate algorithms and communication protocols that allow for the effective exchange of data or information.

In at least one embodiment, backend system 60 can be configured to facilitate registration of wearable electronic device 10. Wearable electronic device 10 may be configured with an assigned phone number (e.g., cellular phone number, Wi-Fi phone number). This phone number can be registered with backend system 60, for example, via a web portal and account. The phone number assigned to wearable electronic device 10 can be linked to the phone number assigned to mobile device 46, thus enabling backend system 60 to provide alerts to wearable electronic device 10 when mobile device 46 receives a phone call or a text message. The user may also select various services from which information can be received by backend system 60 and forwarded to wearable electronic device 10. Such services could include, but are not limited to, email, event/schedule, social network, social offer, friend nearby, and contact information exchange. In at least one embodiment, backend system 60 can link to a calendar service of mobile device 46 and push alerts and invites to wearable electronic device 10. In at least one other embodiment, mobile device 46 could be configured to push at least some information (e.g., contact information) directly to wearable electronic device 10 via a local wireless connection (e.g., Bluetooth™, Wi-Fi). In a further example, backed system 60 may perform a look up and match an incoming phone number with a user's phone contacts to pull the correct information and provide to wearable electronic device 10.

Figure 3:
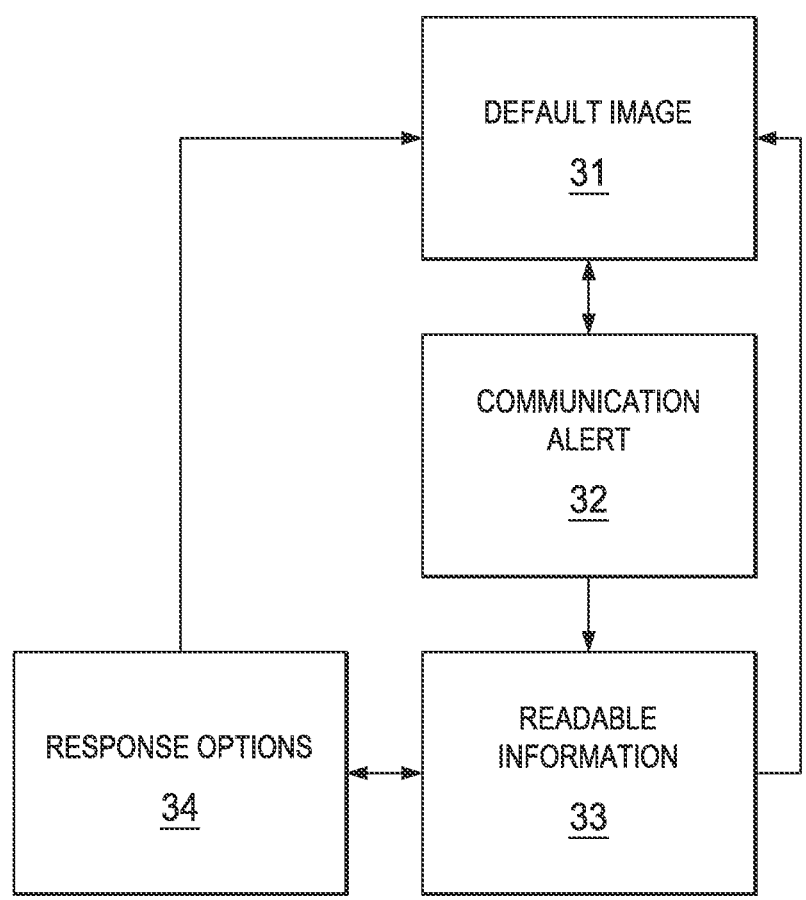
FIG. 3 is a simplified block diagram illustrating example screen transitions that may be associated with a wearable electronic device according to an embodiment of the present disclosure.

Turning to FIG. 3, FIG. 3 is an example of screen transitions that may be associated with one or more embodiments of wearable electronic device 10. In at least one scenario of possible screen transitions, shown in FIG. 3, various displays of information, graphical designs, notifications, etc. may be displayed on display screen 22 of wearable electronic device 10 in accordance with processing in the order of: a default image 31, a communication alert 32, human-readable information 33, and response options 34. Some variations to this order are also illustrated. At least some of these displays may be displayed according to user input or responsive to incoming communications (e.g., incoming phone call information, text message, social media message, etc.).

When wearable electronic device 10 is powered on, default image 31 may be displayed on display screen 22, before communications or user inputs are received. Default image 31 may also be displayed if a predetermined period of time passes (e.g., a pre-configured notification time period) after a communication is received by wearable electronic device 10 without any subsequent user input being received. Default image 31 may also be displayed if a predetermined period of time passes (e.g., a pre-configured user input time period) after user input is received without any subsequent user input or other communications being received. The default image could be graphical, pictorial, geometric, informational, etc., or any combination thereof, in at least one embodiment. In another embodiment, the default image could be a blank power-saving screen.

When a communication (e.g., phone call information, text message, social media message, etc.) is received by wearable electronic device 10 via some network (e.g., WiFi, cellular), then communication alert 32 may be displayed in display screen 22. Default image 31 may be displayed again if the pre-configured notification time period expires without wearable electronic device 10 receiving screen transition input (e.g., user input to view communication details). If screen transition input to view information associated with the communication is received by wearable electronic device 10, then human-readable information 33 can be displayed in screen display 22. Human-readable information 33 can include information that can be read by a human such as text, numbers, graphemes, logograph, etc. If a pre-configured user input time period expires, without any screen transition input being received while human-readable information 33 is displayed, then a screen transition back to default image 31 may be performed.

If a user input is detected while human-readable information 33 is displayed, then response options 34 may be displayed in display screen 22 to allow the user to respond to the communication. Screen transitions may occur to display various other information depending on whether the user selects a response option to respond to the communication. Additionally, a screen transition may be performed to display human-readable information 33, based on user input. If the user responds to the communication, or after a predetermined period of time expires (e.g., pre-configured response time period), then a screen transition to display default image 31 may be performed.

Figure 4E:
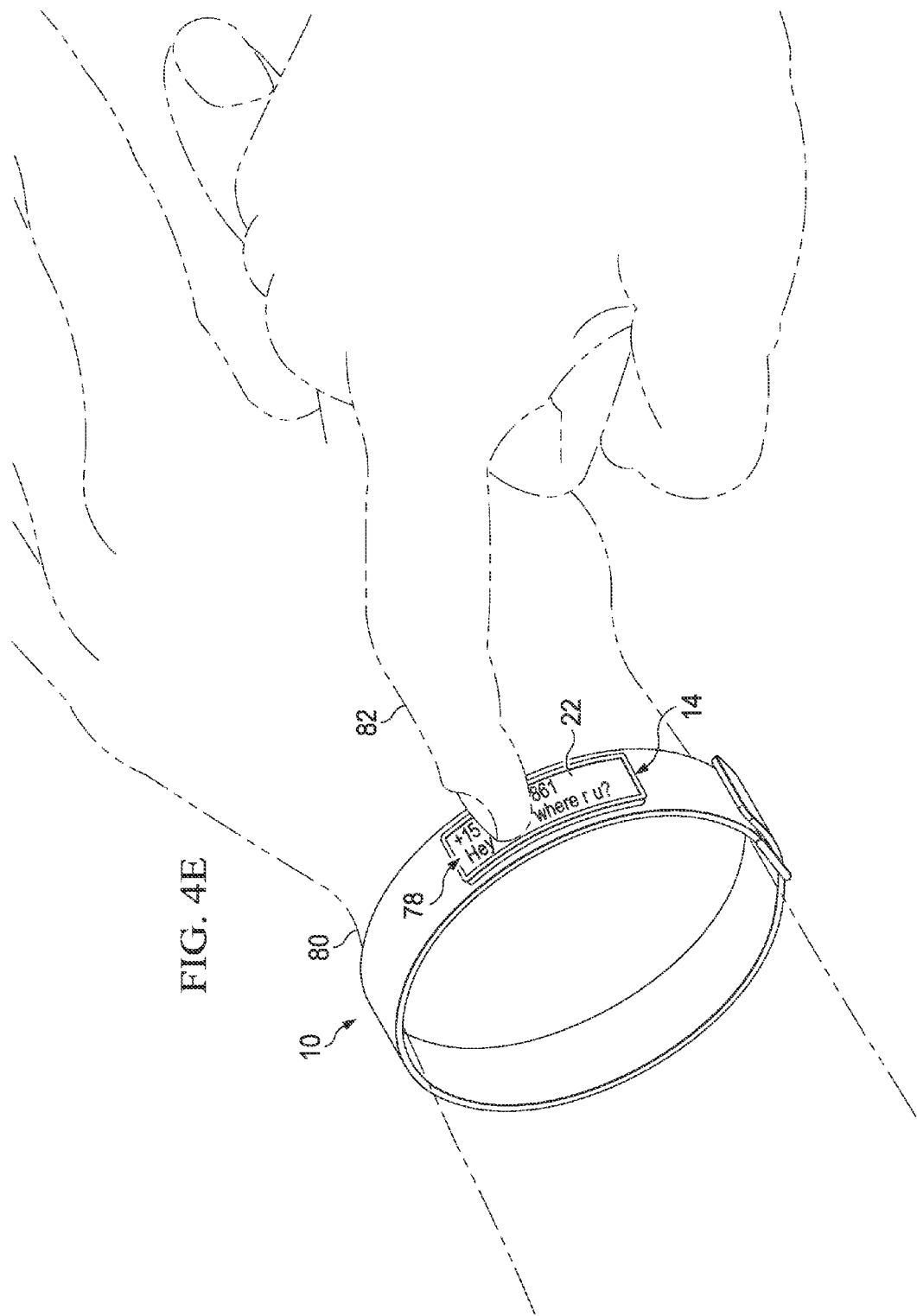
FIG. 4E is a simplified orthographic view illustrating an example wearable electronic device, according to an embodiment of the present disclosure.
Figure 4F:
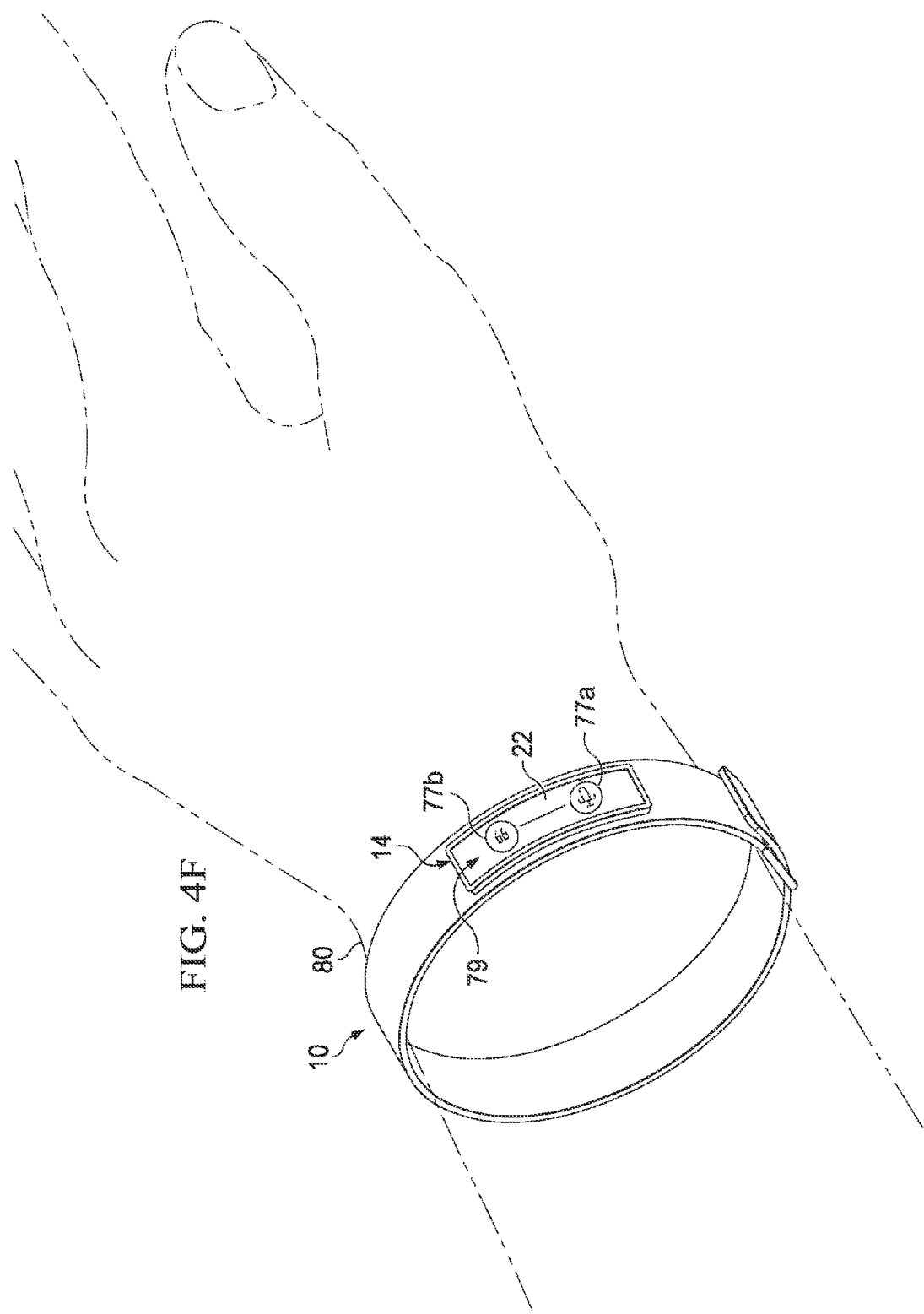
FIG. 4F is a simplified orthographic view illustrating an example wearable electronic device, according to an embodiment of the present disclosure.
Figure 4G:
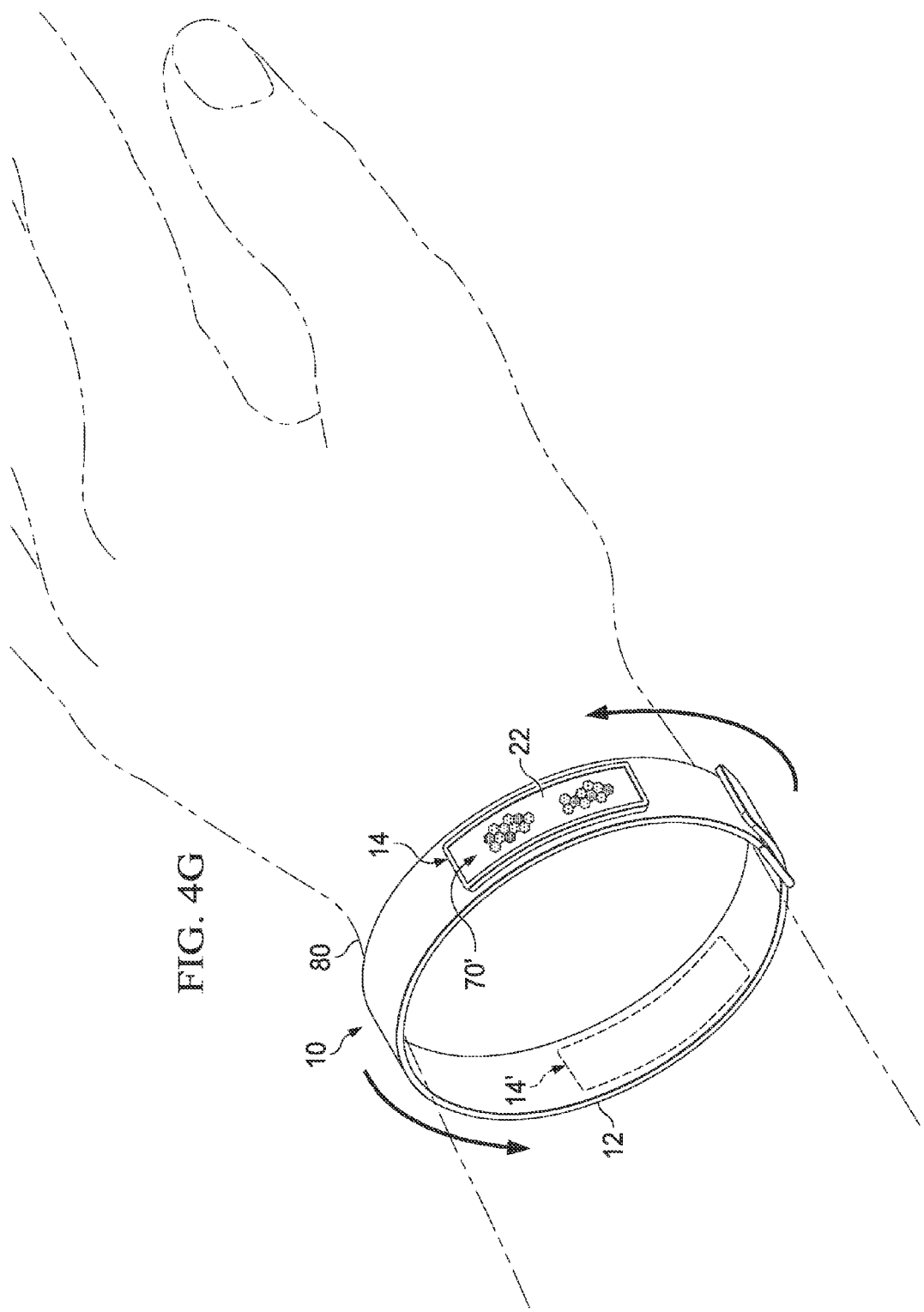
FIG. 4G is a simplified orthographic view illustrating an example wearable electronic device with dual display screens, according to an embodiment of the present disclosure.
Figure 41:
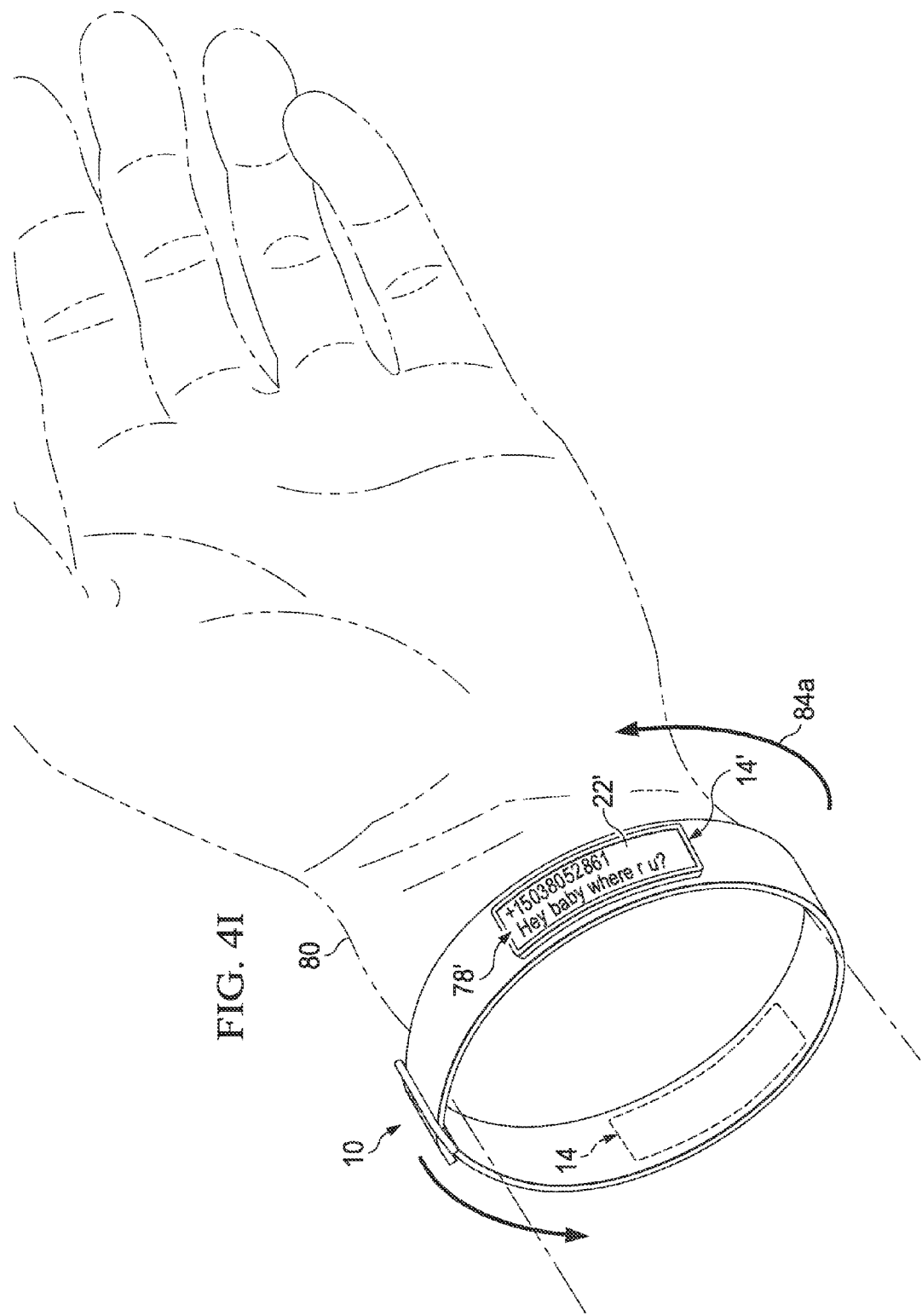
Figure 5A:
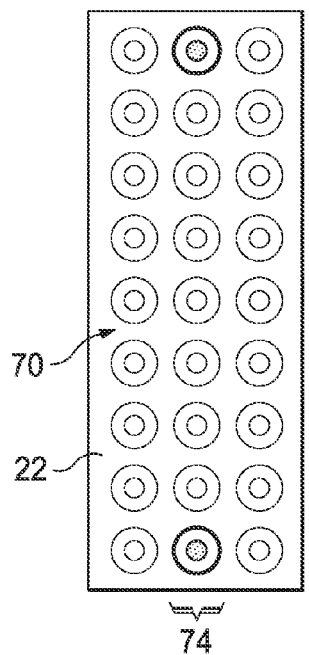
FIGS. 5A-5F show, in sequence, one possible animated notification pattern provided by a wearable electronic device, according to an embodiment of the present disclosure.
Figure 5B:
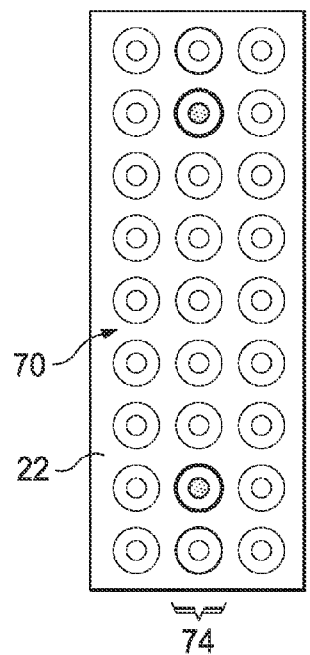
Figure 5C:
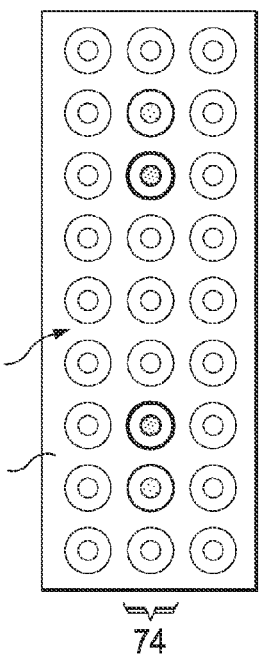
Figure 5D:
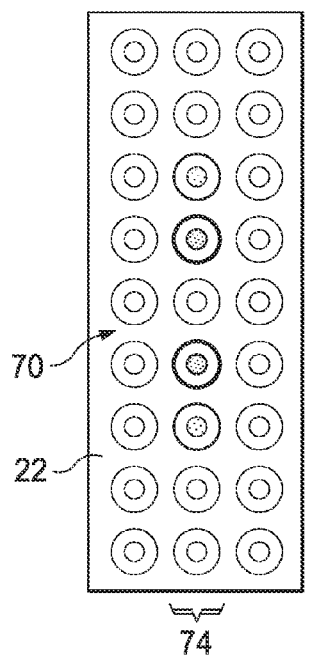
Figure 5E:
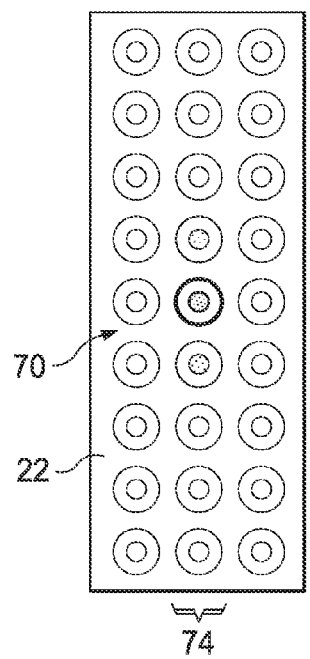
Figure 5F:
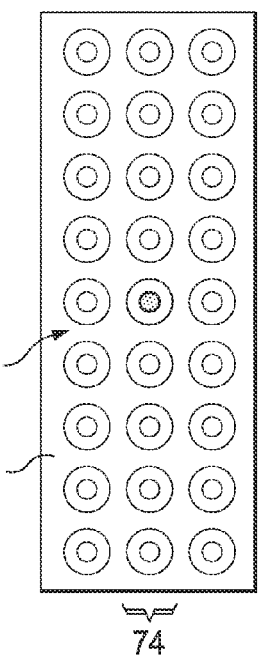

In another embodiment that includes dual display screens, certain displays may be provided on display screen 22 and other displays may be provided on a second display screen (shown in FIGS. 4G-4I). For example, default image 31 and communication alert 32 may be displayed on display screen 22, while human-readable information 33 and response options 34 may be displayed on a second display screen.

Additionally, allowable screen transition input may be different for at least some states. For example, when communication alert 32 is displayed, allowable screen transition input may be a partial rotation of wearable electronic device 10. When human-readable information 33 or response options 34 are displayed in a particular display screen (e.g., display screen 22 or another display screen on wearable device 10), however, allowable screen transition input could potentially include touch input via a touch screen associated with the particular display screen. This example is intended for illustrative purposes only and it will be apparent that wearable electronic device 10 could be configured to allow any type of screen transition input during any state, depending on particular needs and on the sensors and other elements provided in wearable electronic device 10.

Turning to FIGS. 4A-4F, simplified orthographic views illustrate an embodiment of wearable electronic device 10 secured to a user's wrist 80. FIGS. 4A-4F sequentially illustrate at least some of the activities and screen transitions that may occur during an example scenario in which wearable electronic device 10 receives a communication. In this example scenario, the received communication is a text message addressed to mobile device 46. In at least one embodiment, backend system 60 receives the text message, duplicates it, and forwards it to mobile device 46 and to wearable electronic device 10.

As shown in FIG. 4A, wearable electronic device 10 may be secured to user's wrist 80. Display portion 14 of wearable electronic device 10 may be positioned on user's wrist 80 to enable the user to view display screen 22, similar to checking the time on a wrist watch. Sensors, such as motion sensor 25 and fingerprint sensor 24, are not shown in FIG. 4A in order to illustrate other features of wearable electronic device 10. It will be apparent, however, that any of the sensors described herein may be used to facilitate capturing user input.

In at least one embodiment, a default image can be displayed in display screen 22, when wearable electronic device 10 is inactive. Wearable electronic device 10 may be inactive, for example, when it is powered on, but is not receiving any communications via a network and is not receiving any other input from a user. In the example shown in FIG. 4A, the default image includes a current date and time and a small number of icons. It will be apparent that any other image (e.g., graphical, informational, etc.), could be displayed, or that no image may be displayed, when wearable electronic device 10 is inactive.

FIG. 4B illustrates display screen 22 of wearable electronic device 10 displaying an example communication alert 70 when wearable electronic device 10 receives a text message from backend system 60 or possibly from another electronic device (e.g., mobile device 46). In at least one embodiment, the communication alert is a graphic design that alerts the user of the received communication (i.e., the text message in this example scenario), while maintaining the privacy of the text message. In at least one embodiment, the graphic design does not include any textual or numerical information. Also, at least one embodiment of the graphic design covers all or substantially all of display screen 22. Communication alert 70 could be generated using any geometric, pictorial, or other graphic designs, or any combination thereof. In the example shown in FIG. 4B, the graphic design includes a background design that is geometric and symmetrical.

In at least one embodiment, communication alert 70 can be configured to provide a visual language to the user. The visual language may include an arbitrary notification pattern in the graphic design that indicates an attribute of the communication that was received, such as particular type of the communication. Possible notification patterns could include, but are not limited to, a square, an oval, a circle, a horizontal line, a converging or expanding vertical line, an X-shape, a random pattern, etc. Notification patterns could be known to the user, but meaningless to another person. Consequently, if another person views communication alert 70 with a particular notification pattern, the other person would not know the type of communication (e.g., email, text, phone, social media, friend nearby, schedule/event, contact information exchange, etc.) that was received or any other information related to the communication (e.g., sender identity, content of message, etc.). In at least one embodiment, notification patterns could be distinguished from the background of the graphic design by a characteristic (e.g., brightness, color, etc.). Additionally, the notification patterns could be distinguished by animation, in which points along the outline of the pattern are sequentially illuminated and then darkened (or dimmed) to create an appearance of movement along the outline.

In further embodiments, the notification patterns could be tailored to indicate other attributes of the communication, such as a level of importance of the sender and/or the level of importance or urgency of the message content. For example, when a communication is received from a sender having a high level of importance (e.g., spouse, child, parent, employer, etc.), or if message content is critical, the notification pattern could appear brighter. When a communication is received from a sender having a low level of importance (e.g., unknown sender, acquaintances, etc.), or a message content is unimportant, the notification pattern could appear dimmer. In FIG. 4B, several points 76 along an outline of a notification pattern in the graphic design are illuminated.

In at least one embodiment, when a communication alert is displayed in display screen 22, the user can choose to view information related to the received communication or to ignore the notification. Wearable electronic device 10 can be configured to sense touch (e.g., via touch screen), movement (e.g., device rotation, shaking), fingerprint, or other input (e.g., voice command, button press, etc.) provided by the user in response to the communication alert. Such input can be identified as screen transition input to view information associated with the communication. In this example scenario, wearable electronic device 10 includes a motion sensor for capturing movement (e.g., partial rotation of wearable electronic device 10 caused by twisting a wrist) that is responsive to a communication alert when the user wants to view the communication details.

FIG. 4C is a simplified orthographic view of wearable electronic device 10, having a motion sensor, such as motion sensor 25. In at least one embodiment, the motion sensor can be configured to provide measurements of detected movements of wearable electronic device 10. Wearable electronic device 10 can include logic configured to identify input data of a particular movement as indicative of a screen transition input. This particular movement could be a partial rotation of wearable electronic device 10. Such movement could be caused by a user twisting his wrist until his palm faces upward when wearable electronic device 10 is secured to the wrist. This wrist action can cause a partial rotation of wearable electronic device 10 generally about an axis defined by a forearm 85 and wrist 80 of the user, as shown in FIG. 4C. The rotation may be counterclockwise, as shown by directional arrow 84*a*, from the perspective of the user viewing forearm 85 from an elbow to fingertips. In other embodiments, the particular movement that indicates screen transition input when a communication alert is displayed could be a clockwise rotational movement, a vertical movement, a horizontal movement, or any other movement having a particular direction and acceleration that can be measured by the motion sensor.

FIG. 4D is a simplified orthographic view of wearable electronic device 10 secured to user's wrist 80, when the user's wrist has been rotated back from the position shown in FIG. 4C, as indicated by directional arrow 84*b*. As shown in FIG. 4D, display portion 14 is positioned to enable user to view display screen 22 as if checking the time of a wrist watch. The graphic design of the communication alert (shown in FIG. 4B) has been transitioned to a screen displaying communication details 78 that includes human-readable information associated with the received communication. In this scenario, the content of a text message is displayed in display screen 22. Other examples of communication details can include, but are not limited to, information related to an incoming phone call alert, transcribed voice message associated with an incoming phone call alert, email content associated with an email alert, event/schedule information associated with an event/schedule alert, social network message associated with a social network alert, social offer (e.g., view and redeem) information associated with a social offer alert, information related to a friend nearby alert, and new contact information associated with a contact information exchange alert.

FIG. 4E is a simplified orthographic view of wearable electronic device 10 secured to user's wrist 80, with communication details 78 provided in display screen 22. Wearable electronic device 10 can be configured to receive any suitable user input on a touch screen of display portion 14 (e.g., swiping, tapping, touching and holding, etc.) as a screen transition input. The screen transition input represents a command to transition the current display in the display screen to a display of options to respond to the received communication. In the example illustrated in FIG. 4E, the user is touching the touch screen of display portion 14 using a finger 82. In other embodiments, wearable electronic device 10 could be configured to receive other types of user input (e.g., voice commands, movement, gestures, etc.) as screen transition input to view the response options.

FIG. 4F is a simplified orthographic view of wearable electronic device 10 secured to user's wrist 80, with response options 79 displayed in display screen 22. Response options 79 may offer one or more response options for the user to respond to the received communication, which is a text message in this scenario. For example, icons 77*a* and 77*b* indicating the available response options (e.g., recorded voice message, response text message) may be displayed in display screen 22. Wearable electronic device 10 may be configured to allow the user to select one or more of the options via the touch screen of display portion 14. In other embodiments, wearable electronic device 10 may be configured to allow other user input (e.g., voice commands, movement, gestures, etc.) to select a desired response option.

Turning to FIGS. 4G-4I, simplified orthographic views illustrate a dual display screen embodiment of wearable electronic device 10 secured to user's wrist 80. FIGS. 4G-4I sequentially illustrate at least some of the activities and screen transitions that may occur during an example scenario in which wearable electronic device 10 receives a communication. Screen transitions in a dual display screen embodiment may be similar to those in a single display screen embodiment (e.g., FIGS. 4A-4F). In a dual display screen embodiment, however, one or more screen transitions may occur in one display screen and/or may occur from one display screen to another display screen. Additionally, certain screen transition inputs (e.g., touch input) may be associated with a particular one of the display screens during a particular state in a dual display screen embodiment. In the example scenario illustrated in FIGS. 4G-4I, the received communication is a text message addressed to mobile device 46. In at least one embodiment, backend system 60 receives the text message, duplicates it, and forwards it to mobile device 46 and to wearable electronic device 10.

As shown in FIG. 4G, wearable electronic device 10 includes first display screen 22 coupled to display portion 14, and display portion 14 coupled to strap portion 22, as previously described herein. For ease of illustration, screen display 22 and display portion 14 are also referred to herein as "first display screen 22" and "first display portion 14", respectively. Wearable electronic device 10 of FIG. 4G also includes a second display portion 14', which may be configured in the same or similar manner as first display portion 14. Second display portion 14' may be coupled to (e.g., disposed within/on and/or supported by) strap portion 12. First and second display portions 14 and 14' may be disposed along strap portion 12 such that when wearable device 10 is secured to user's wrist 80, first display portion 14 can be positioned adjacent to a top side of user's wrist 80, and second display portion 14' can be positioned adjacent to a bottom side of user's wrist 80. Sensors, such as motion sensor 25 and fingerprint sensor 24, are not shown in FIG. 4G in order to illustrate other features of wearable electronic device 10 with dual display screens. It will be apparent, however, that any of the sensors described herein may be used to facilitate capturing user input.

A default image (shown in FIG. 4A) may be displayed in first display screen 22, when wearable device is inactive, or no image may be displayed when wearable device is inactive. FIG. 4G illustrates display screen 22 of wearable electronic device 10 displaying an example communication alert 70' when wearable electronic device 10 receives a text message from backend system 60 or possibly from another electronic device (e.g., mobile device 46). Communication alert 70' is another illustrative example of a possible graphical design that may be used to alert a user of a communication received by wearable electronic device 10.

In at least one embodiment, when communication alert 70' is displayed in display screen 22, the user can choose to view information related to the received communication or to ignore the notification. Wearable electronic device 10 can be configured to sense touch (e.g., via touch screen), movement (e.g., device rotation, shaking), fingerprint, or other input (e.g., voice command, button press, etc.) provided by the user in response to communication alert 70'. Such input can be identified as screen transition input to view information associated with the communication. In this example scenario, wearable electronic device 10 includes a motion sensor as previously described herein for capturing movement (e.g., partial rotation of wearable electronic device 10 caused by twisting a wrist) that is responsive to a communication alert.

FIG. 4H is a simplified orthographic view illustrating a counterclockwise, partial rotation of user's wrist 80. Logic may be configured in wearable electronic device 10 to identify input data corresponding to the captured movement. The input data can be identified as indicative of a screen transition input to view the communication details. When input data is identified as screen transition input, then first display screen 22 can be deactivated and communication alert 70' can be removed, for example, by transitioning to the default image or transitioning to a blank screen. In addition, the identification of the screen transition input can cause second display screen 22' to be activated such that information associated with the communication is displayed in second display screen 22'. As previously described herein, any other suitable movements could also, or alternatively, be used to indicate screen transition input when a communication alert is displayed.

FIG. 4I is a simplified orthographic view of wearable electronic device 10 secured to user's wrist 80, when the user's wrist has been partially rotated to reveal a bottom side of user's wrist 80 and second display screen 22'. As shown in FIG. 4I, second display portion 14' is positioned to enable the user to view second display screen 22' when the user's wrist is flipped over. The graphic design of communication alert 70' displayed in first display screen 22 (shown in FIG. 4G) has been removed from first display screen 22, and communication details 78' are displayed in display screen 22'. Communication details 78' can include human-readable information associated with the received communication. In this scenario, the content of a text message is displayed in second display screen 22'. Other types of communication details may also be displayed in second display screen 22' depending on the particular communication received by wearable electronic device 10.

Wearable electronic device 10 may also be configured to receive any suitable user input that represents a screen transition input to view response options on second display screen 22'. Suitable user input could include, for example, touch input on a touch screen of display portion 14' (e.g., swiping, tapping, touching and holding, etc.). The screen transition input represents a command to transition the current display of second display screen 22' to a display of response options for the received communication, as previously described herein with reference to FIGS. 4E and 4F. In other embodiments, wearable electronic device 10 could be configured to receive other types of user input (e.g., voice commands, movement, gestures, etc.) as screen transition input to view the response options on second display screen 22'. In at least one embodiment, response options may be displayed and selected in second display screen 22' as previously described herein, for example, with reference to first display screen 22 in FIGS. 4E and 4F.

It is also important to note that when the default image is displayed, and possibly when one or more other images are displayed, a user may have certain options in addition to receiving and responding to communication alerts. Wearable electronic device 10 may be configured to detect any input, based on particular needs or preferences, to call up a new action. Such actions could include, but are not limited to, checking-in to social networks, pinning a location/place, initiating a contact information exchange, changing 'broadcast' settings, changing 'listening' settings, and/or creating a voice memo.

Turning to FIGS. 5A-5F, FIGS. 5A-5F illustrate example communication alert 70 displayed in display screen 22 of wearable electronic device 10. FIGS. 5A-5F each represent a different instance in time over a period of time in which a notification pattern 74 is displayed in the graphic design by sequentially illuminating and darkening points in the pattern. The sequential illuminating and darkening of points in the pattern over a period of time is referred to herein as 'animation' and can create an appearance of movement along the outline of the pattern.

In at least one embodiment, notification patterns can be designs that represent different types of alerts. A notification pattern can be any design that is recognizable to a user and distinguishable from other notification patterns. In the example illustration of FIGS. 5A-5F, notification pattern 74 is a converging vertical line and represents, for example, a text message alert. In other examples, each unique notification pattern (e.g., a square, an oval, a circle, an X-shape, a vertical line appearing to expand, a horizontal line, a random pattern, etc.) could represent a different alert. The alerts can include, but are not limited to, an incoming phone call alert, a text message alert, an email alert, an event/schedule alert, a social network alert, a social offer alert, a friend nearby alert, and contact information exchange alert.

In at least one embodiment, the notification pattern could also be visually distinguishable based on a level of importance of the sender and/or based on the urgency of the communication. For example, illuminated points in the notification pattern could appear brighter or a different color when a communication is received from an important sender and/or if message content of the communication was urgent.

In at least one embodiment, notification patterns may be configurable by a user. For example, a user may select which notification pattern corresponds to which type of communication. In addition, the shape of the pattern, the brightness, the color, and any other possible distinguishing characteristics may be configured to represent any of the possible attributes of a received communication. For example, types of communications may be distinguishable by color of the notification pattern rather than by the shape/animation of the pattern itself.

As illustrated herein, and particularly with reference to the examples of FIGS. 4G-4I, the heterogeneous display screens of wearable electronic device 10 may allow improved social interactions and desirability by ensuring aesthetic elements are prominent and providing the convenience of wearability to stay connected in a non-disruptive manner. The dual display screens allow a user to know what is happening via incoming communications that include communications intended for the user's other mobile electronic devices and that also include messages/alerts from selected services. The dual display screens provide just enough information to enable the user to determine whether a particular event is important enough to act on at that moment, without the need for manipulating a larger handheld device. A single display screen utilizing the communication alerts and screen transition inputs as described herein, can offer similar advantages.

Turning to FIG. 6, FIG. 6 is a flowchart of a possible flow 600 that may be associated with embodiments described herein. In at least one embodiment, logic in the form of one or more sets of operations correspond to activities of FIG. 6. Wearable electronic device 10 may comprise means, including one or more processors (further described herein at least with reference to FIGS. 7 and 8), for performing the operations.

Flow 600 may begin at 602, where wearable electronic device 10 receives a communication via a wireless network. The communication could be received, for example, via a cellular or Wi-Fi network. At 604, a communication alert is selected to be displayed on display screen 22 to indicate to the user that wearable electronic device 10 has received a communication. The communication alert could also be selected based on one or more attributes of the received communication. A notification pattern in the communication alert may indicate one or more of the attributes including, but not necessarily limited to, the type of communication (e.g., email, text message, social media message, etc.), the importance of the sender, and the urgency of the communication.

In at least one embodiment, the communication alert is a graphic design that protects the privacy of the communication. For example, any geometric designs, pictorial designs, photographs, diagrams, symbols, combinations thereof, etc. that do not convey private information associated with the received communication (e.g., sender name, message content, phone numbers, etc.) may be used to indicate wearable electronic device 10 has received a communication. In one or more embodiments, the graphic design includes a background design and a notification pattern. In at least some embodiments, the background design of each communication alert of a wearable electronic device is the same, with the respective notification patterns distinguishing the communication alerts from one another. Providing the same background design can provide a common visual cue to a user that wearable electronic device 10 has received a communication for the user. This may be particularly helpful when the number of attributes and combinations thereof, that are indicated by changes in the notification patterns grow.

The graphic designs can be pre-configured by a user, or pre-configured as a default setting. For example, a user may select a common background design (or no background design) and then configure notification patterns, and possibly characteristics of the notification patterns (e.g., brightness, color, speed of animation, etc.), to correspond to different attributes of received communications. For example, the shape of a notification pattern may correspond to a type of communication, a brightness of a notification pattern may correspond to the importance of the sender, and a color of the notification pattern may correspond to the urgency of the message. It will be readily apparent that these examples are for illustrative purposes only and the notification pattern and its features could be configured to represent any desired combination of one or more attributes of received communications.

In order for wearable electronic device 10 to identify a sender's importance level, the user may also categorize possible senders (e.g., from the user's email contacts, from the user's phone contacts, etc.), or groups of possible senders, based on their importance level. These categorizations may be stored in any suitable memory (e.g., memory in wearable electronic device 10, memory in backend system 60) and structure (e.g., table, list, address book, etc.) Although any number of importance levels could be configured, a smaller selection of levels may increase the ease with which a user learns the meaning of the notification patterns and their various characteristics. Wearable electronic device 10 can also include a natural language processor to detect a level of urgency from text and/or tags in a received communication, and the corresponding notification pattern and/or its characteristics may be selected accordingly.

At 606, the selected communication alert is provided for display on display screen 22 of wearable electronic device 10. In at least one embodiment, the communication alert does not display private or distracting textual information associated with the communication, and thus, may not be understood by anyone other than the user. This may be particularly useful to maintain privacy in crowded settings. For example, a user who receives a text message while riding in a crowded subway can easily find out what type of communication they are receiving and possibly the urgency of the message without divulging any private information to persons nearby.

At 608, the communication alert may be displayed on display screen 22 for a pre-configured notification time period or until the user responds to the communication alert by providing allowable screen transition input. It will be apparent that the communication alert may also cease to be displayed if wearable electronic device is powered off by the user or otherwise loses power. If the pre-configured notification time period expires, then at 620, a default image may be provided for display on display screen 22. The default image can replace the communication alert. Thus, at 622, a transition can be made in display screen 22 to display the default image, which could potentially be a blank screen saver.

If input data from an input device (e.g., motion sensor, fingerprint sensor, etc.) is received prior to the expiration of the notification time period, then at 612, a determination is made as to whether the input data is indicative of screen transition input in the current state (i.e., when the communication alert is being displayed). For example, if allowable screen transition input is defined as a partial rotation of wearable electronic device 10, then input data indicating the device is being shaken is not recognized as screen transition input and therefore, is not an allowed response to the communication alert. Thus, if the input data is not an allowed response, then the communication alert may continue to be displayed at 608 until more input data is received or until the notification time period expires.

If it is determined at 612, that the input data is indicative of as screen transition input in the current state (i.e., when the communication alert is being displayed), then at 614, information associated with the received communication may be provided for display on a display screen of wearable electronic device 10. In a single display screen embodiment of wearable electronic device 10, at 614, the information may be provided for display in display screen 22. The information can replace the communication alert in display screen 22. At 616, a transition can be made in display screen 22 to display the information associated with the received communication.

In a dual display screen embodiment of wearable electronic device 10, at 614, the information may be provided for display in second display screen 22'. First display screen 22 can be deactivated and the communication alert can be removed. At 616, second display screen 22' can be activated to display the information associated with the received communication.

At 618, options may be provided via display screen 22 (e.g., in a single display screen embodiment) or via display screen 22' (e.g., in a dual display screen embodiment) to enable the user to respond to the received communication. The options may be provided with the displayed information in at least one embodiment. However, due to the small screen area of the display screen, the information may be displayed without response options and configured to allow the user to provide input (e.g., via touch screen, voice command, etc.) to wearable electronic device 10 to cause another screen transition to display the response options in the appropriate display screen (e.g., 22 or 22').

Figure 7:
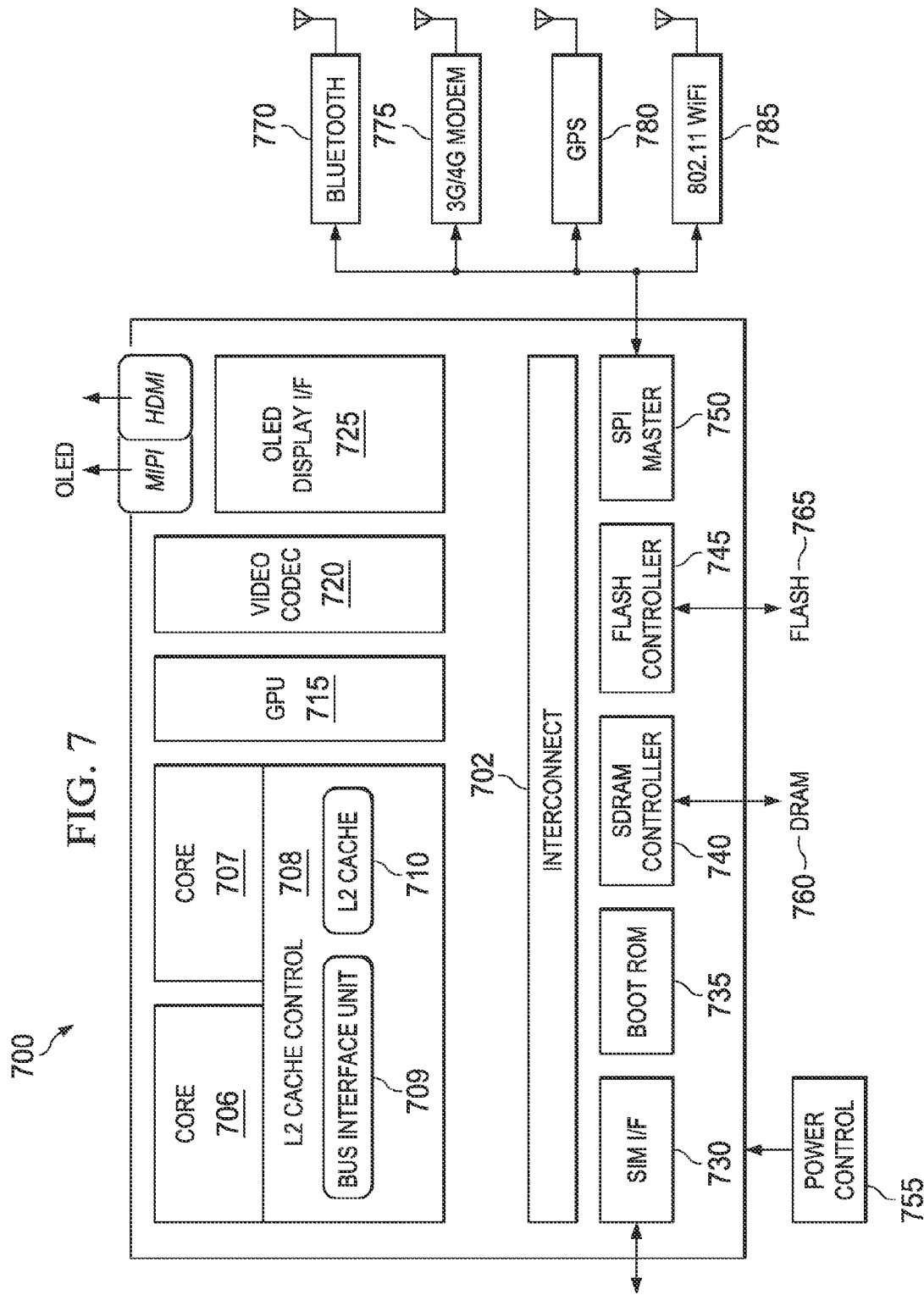
FIG. 7 is a simplified block diagram associated with an example ARM ecosystem on chip (SOC) of the present disclosure.

FIG. 7 is a simplified block diagram associated with an example ARM ecosystem SOC 700 of the present disclosure. At least one example implementation of the present disclosure can include integration of the wearable electronic device features discussed herein and an ARM component. For example, the example of FIG. 7 can be associated with any ARM core (e.g., A-9, A-15, etc.). Further, the architecture can be part of any type of wearable electronic device, tablet, smartphone (inclusive of Android™ phones, i-Phones™), i-Pad™, Google Nexus™, Microsoft Surface™, video processing components, laptop computer (inclusive of any type of notebook), Ultrabook™ system, any type of touch-enabled input device, etc.

In this example of FIG. 7, ARM ecosystem SOC 700 may include multiple cores 706-707, an L2 cache control 708, a bus interface unit 709, an L2 cache 710, a graphics processing unit (GPU) 715, an interconnect 702, a video codec 720, and an organic light emitting diode (OLED) display I/F 725, which may be associated with mobile industry processor interface (MIPI)/high-definition multimedia interface (HDMI) links that couple to an OLED.

ARM ecosystem SOC 700 may also include a subscriber identity module (SIM) I/F 730, a boot read-only memory (ROM) 735, a synchronous dynamic random access memory (SDRAM) controller 740, a flash controller 745, a serial peripheral interface (SPI) master 750, a suitable power control 755, a dynamic RAM (DRAM) 760, and flash 765. In addition, one or more embodiments include one or more communication capabilities, interfaces, and features such as instances of Bluetooth™ 770, a 3G/4G modem 775, a global positioning system (GPS) 780, and an 802.11 WiFi 785.

In operation, the example of FIG. 7 can offer processing capabilities, along with relatively low power consumption to enable computing of various types (e.g., mobile computing). In addition, such an architecture can enable any number of software applications (e.g., Android™, Adobe® Flash® Player, Java Platform Standard Edition (Java SE), JavaFX, Linux, Microsoft Windows Embedded, Symbian and Ubuntu, etc.). In at least one embodiment, the core processor may implement an out-of-order superscalar pipeline with a coupled low-latency level-2 cache.

Figure 8:
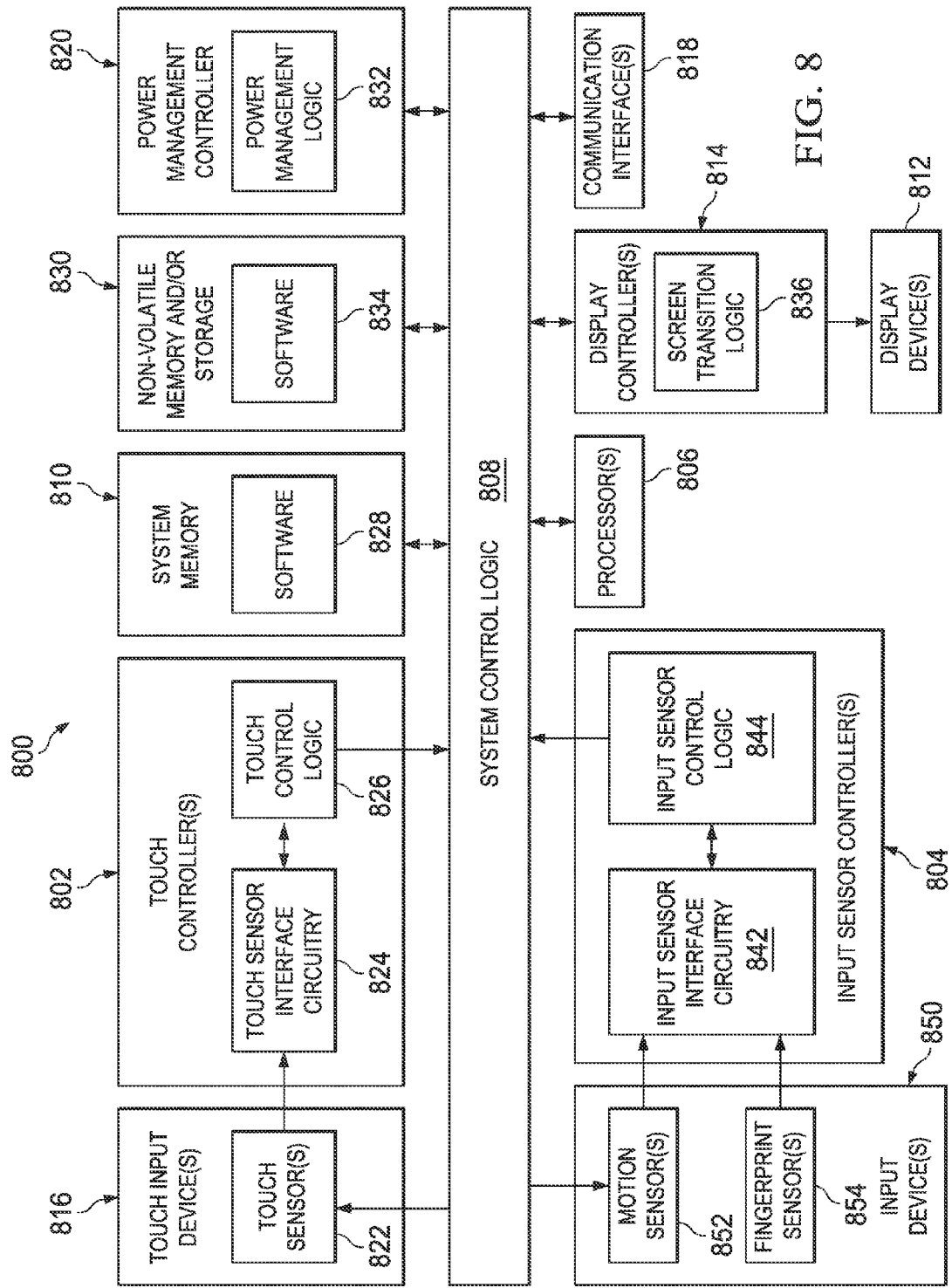
FIG. 8 is a simplified block diagram illustrating example logic that may be used to execute activities associated with the present disclosure.

Turning to FIG. 8, FIG. 8 is a simplified block diagram illustrating potential electronics and logic that may be associated with any embodiments of the wearable electronic device discussed herein. Certain electronics and logic of FIG. 8 can be discrete or integrated into a System on a Chip (SOC) for example, as disclosed with reference to FIG. 7. Instead of wearable electronic devices, at least some alternative implementations could include mobile phones, tablets, phablets, etc.

In at least one example embodiment, system 800 can include touch controller(s) 802, input sensor controller(s) 804, one or more processors 806, system control logic 808 coupled to at least one of processor(s) 806, system memory 810 coupled to system control logic 808, non-volatile memory and/or storage device(s) 830 coupled to system control logic 808, display controller(s) 814 coupled to system control logic 808, display controller(s) 814 coupled to display device(s) 812, power management controller 820 coupled to system control logic 808, and/or communication interfaces 818 coupled to system control logic 808.

System control logic 808, in at least one embodiment, can include any suitable interface controllers to provide for any suitable interface to at least one processor 806 and/or to any suitable device or component in communication with system control logic 808. System control logic 808, in at least one embodiment, can include one or more memory controllers to provide an interface to system memory 810. System memory 810 may be used to load and store data and/or instructions, for example, for system 800. System memory 810, in at least one embodiment, can include any suitable volatile memory, such as suitable dynamic random access memory (DRAM) for example. System control logic 808, in at least one embodiment, can include one or more I/O controllers to provide an interface to display device 812, touch controller(s) 802, input sensor controller(s) 804, and non-volatile memory and/or storage device(s) 830.

Non-volatile memory and/or storage device(s) 830 may be used to store data and/or instructions, for example within software 834. Non-volatile memory and/or storage device(s) 830 may include any suitable non-volatile memory, such as flash memory for example, and/or may include any suitable non-volatile storage device(s), such as one or more hard disc drives (HDDs), solid state drives (SSDs), etc. for example.

Power management controller 820 may include power management logic 832 configured to control various power management and/or power saving functions. In at least one example embodiment, power management controller 820 is configured to reduce the power consumption of components or devices of system 800 that may either be operated at reduced power or turned off when the wearable electronic device is in an inactive state (e.g., not being accessed by user, not receiving communications, etc.). For example, in at least one embodiment, when the wearable electronic device is in an inactive state, power management controller 820 performs one or more of the following: power down the unused portion of the display and/or any backlight associated therewith; allow one or more of processor(s) 806 to go to a lower power state if less computing power is required in the closed configuration; and shutdown any devices and/or components (e.g., wireless module) that may be unused when an electronic device is in an inactive state.

Communications interface(s) 818 may provide an interface for system 800 to communicate over one or more networks and/or with any other suitable device. Communications interface(s) 818 may include any suitable hardware and/or firmware. Communications interface(s) 818, in at least one embodiment, may include, for example, a network adapter, a wireless network adapter, a telephone modem, and/or a wireless modem.

One or more display controllers 814 generate screen data for displaying images on one or more respective display screens of display devices 812 (e.g., display screen 22, display screen 22' of wearable electronic device 10). In at least one embodiment, a first display controller generates screen data for displaying images on first display screen 22 and a second display controller generates screen data for displaying images on second display screen 22'. Certain screen data (e.g., communication alert data) may be generated by the first display controller when a communication is received on wearable electronic device 10 and may be displayed on a display screen, such as first display screen 22. Certain other screen data (e.g., communication information) may be generated by the second display controller according to input data received from a touch input device (e.g., one of touch input devices 816) or one of input devices 850 (or another input device not shown). This other screen data may be displayed on a display screen, such as first display screen 22 in a single display embodiment or second display screen 22' in a dual display embodiment. The input data can be processed by logic stored in software, firmware, hardware, or any combination thereof, and may include one or more operations previously described herein for example, with reference to FIG. 6. One or more display controllers 814 can also include screen transition logic 836, which can transition one screen image to another screen image within a single display device (e.g., animation images of a communication alert communication alert to human-readable information in a single display embodiment, communication information to response options, etc.). Display controller(s) 814 can provide the screen data to the appropriate display device(s) 812.

System control logic 808, in at least one embodiment, can include one or more I/O controllers to provide an interface to any suitable input/output device(s) such as, for example, an audio device (not shown) to help convert sound into corresponding digital signals and/or to help convert digital signals into corresponding sound, a camera or a camcorder.

For at least one embodiment, at least one processor 806 may be packaged together with logic for one or more controllers of system control logic 808. In at least one embodiment, at least one processor 806 may be packaged together with logic for one or more controllers of system control logic 808 to form a System in Package (SiP). In at least one embodiment, at least one processor 806 may be integrated on the same die with logic for one or more controllers of system control logic 808. For at least one embodiment, at least one processor 806 may be integrated on the same die with logic for one or more controllers of system control logic 808 to form a System on Chip (SoC).

For touch control, touch controller(s) 802 may include touch sensor interface circuitry 824 and touch control logic 826. A touch controller and its corresponding touch input device 816 is described herein with reference to a particular display device 812. Depending on the embodiment, however, a different touch controller and corresponding touch device 816 may be configured for each display device 812 (e.g., display screen 22, display screen 22'). Touch sensor interface circuitry 824 may be coupled to one or more touch sensor(s) 822 to detect touch input(s) over a first touch surface layer and a second touch surface layer of a particular display device 812. Touch sensor interface circuitry 824 may include any suitable circuitry that may depend, for example, at least in part on the touch-sensitive technology used for the particular touch input device 816, which may include one or more touch sensor(s) 822. Touch sensor interface circuitry 824, in one embodiment, may support any suitable multi-touch technology. Touch sensor interface circuitry 824, in at least one embodiment, can include any suitable circuitry to convert analog signals corresponding to a first touch surface layer and a second surface layer into any suitable digital touch input data. Suitable digital touch input data for at least one embodiment may include, for example, touch location or coordinate data.

Touch control logic 826 may be coupled to help control touch sensor interface circuitry 824 in any suitable manner to detect touch input over a first touch surface layer and a second touch surface layer of a particular display device. Touch control logic 826 for at least one embodiment may also be coupled to output, in any suitable manner, digital touch input data corresponding to touch input detected by touch sensor interface circuitry 824. Touch control logic 826 may be implemented using any suitable logic, including any suitable hardware, firmware, and/or software logic (e.g., non-transitory tangible media), that may depend, for example, at least in part on the circuitry used for touch sensor interface circuitry 824. Touch control logic 826 for at least one embodiment may support any suitable multi-touch technology.

Touch control logic 826 may be coupled to output digital touch input data to system control logic 808 and/or at least one processor 806 for processing. At least one processor 806 for at least one embodiment may execute any suitable software to process digital touch input data output from touch control logic 826. Suitable software may include, for example, any suitable driver software and/or any suitable application software. As illustrated in FIG. 8, system memory 810 may store software 828, which is invoked and/or currently executing, and non-volatile memory and/or storage device 830 may store software 834.

For other input sensor controls, one or more input sensor controllers 804 may include input sensor interface circuitry 842 and input sensor control logic (e.g., for motion sensor control, for fingerprint sensor control, audio sensor control, button press control, for other biometric sensors' control, etc.). Input sensor interface circuitry 842 may be coupled to an input device (e.g., motion sensor 852, fingerprint sensor 854, microphone (not shown), button (not shown), other biometric sensors (not shown), etc.) to control the operation of the particular input device and receive the particular inputs (e.g., movement measurements, captured fingerprints, voice commands, button press signals, voice patterns, eye retinas and/or irises, facial features, hand features, palm prints, pulse features, vein patterns, etc.). Input sensor circuitry 842 may include any suitable circuitry that may depend, for example, at least in part on the particular technology (e.g., motion sensor technology, fingerprint sensor technology, microphone technology, button press technology, other biometric technology, etc.) used for the particular input device. For example, input sensor interface circuitry 842 for a fingerprint sensor may support multi-fingerprint capturing technology and may be provided in one or more display devices 812 or another separate fingerprint capturing surface. In another example, input sensor interface circuitry 842 for a motion sensor may support both accelerometer measurements and gyroscope measurements. Depending on the particular input sensor used, input sensor interface circuitry 842 may include suitable circuitry to convert analog signals to into any suitable digital data.

Input sensor control logic 844 may be coupled to control input sensor interface circuitry 842 in any suitable manner to control the particular input sensor (e.g., motion sensor 852, fingerprint sensor 854, etc.) and to capture appropriate data. Input sensor control logic 844, for at least one embodiment, may also be coupled to output in any suitable manner digital data detected by input sensor interface circuitry 842. Input sensor control logic 844 may be implemented using any suitable logic, including any suitable hardware, firmware, and/or software logic (e.g., non-transitory tangible media), that may depend, for example, at least in part on the circuitry used for input sensor interface circuitry 842. Input sensor control logic 844, for at least one embodiment, may support any suitable motion detection technology, any suitable multi-fingerprint capturing technology, and any other technology associated with the particular sensor being used.

Input sensor control logic 844 may be coupled to output digital data (e.g., movement data, fingerprint data, voice data, button press data, etc.) to system control logic 808 and/or at least one processor 806 for processing. At least one processor 806 for at least one embodiment may execute any suitable software to process the digital data output from input sensor control logic 844. For example, digital data may, in one or more embodiments, be processed to determine if the digital data is indicative of allowable screen transition input in the current state (e.g., when a particular screen being displayed). Suitable software may include, for example, any suitable driver software and/or any suitable application software. As illustrated in FIG. 8, system memory 810 may store suitable software 828 and/or non-volatile memory and/or storage device(s) may store any suitable software 834.

Note that in some example implementations, the functions outlined herein may be implemented in conjunction with logic that is encoded in one or more tangible, non-transitory computer readable storage media (e.g., embedded logic provided in an application-specific integrated circuit (ASIC), in digital signal processor (DSP) instructions, software [potentially inclusive of object code and source code] to be executed by a processor, or other similar machine, etc.). In some of these instances, memory elements can store data used for the operations described herein. This can include the memory elements being able to store software, logic, code, or processor instructions that are executed to carry out the activities described herein. A processor can execute any type of instructions associated with the data to achieve the operations detailed herein. In one example, the processors could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), a DSP, an erasable programmable read only memory (EPROM), electrically erasable programmable read-only memory (EEPROM)) or an ASIC that can include digital logic, software, code, electronic instructions, or any suitable combination thereof.

It is imperative to note that all of the specifications, dimensions, and relationships outlined herein (e.g., height, width, length, materials, etc.), in addition to other protocols and relationships (e.g., specific commands, timing intervals, etc.) have been offered for purposes of example and teaching only. Each of these data may be varied considerably without departing from the spirit of the present disclosure, or the scope of the appended claims. The specifications apply to non-limiting examples and, accordingly, they should be construed as such.

It is also important to note that the blocks in the flow diagrams illustrate only some of the possible signaling scenarios and patterns that may be executed by, or within, the circuits discussed herein. Some of these blocks may be deleted or removed where appropriate, or these operations may be modified or changed considerably without departing from the scope of teachings provided herein. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by the present disclosure in that any suitable arrangements, chronologies, configurations, and timing mechanisms may be provided without departing from the teachings provided herein.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

OTHER NOTES AND EXAMPLES

The following examples pertain to embodiments in accordance with this Specification. Note that all optional features of the apparatuses and systems described above may also be implemented with respect to the method or process described herein and specifics in the examples may be used anywhere in one or more embodiments.

Example 1 is a wearable electronic device, comprising a first display screen; a second display screen; and logic, at least a portion of which is implemented in hardware, the logic configured to: receive a communication over a wireless network; display, in the first display screen, a communication alert representing the communication, wherein the communication alert is a graphic design; receive input data indicative of a screen transition input to view information associated with the communication; and display, in the second display screen, the information associated with the communication.

In Example 2, the subject matter of Example 1 can optionally include the logic configured to select the communication alert to be displayed, where the graphic design includes a notification pattern indicating one or more attributes of the communication.

In Example 3, the subject matter of Example 2 can optionally include one of the attributes being a type of the communication, where the type is one of a plurality of types of communication.

In Example 4, the subject matter of any one of Examples 2-3 can optionally include the notification pattern being animated.

In Example 5, the subject matter of any one of Examples 2-4 can optionally include one of the attributes being one of a level of importance of a sender of the communication and a level of urgency of the communication.

In Example 6, the subject matter of Example 3 can optionally include the types of communication including one or more of a phone call message, a text message, an electronic mail message, an event or schedule message, a social network message, a social offer message, a friend nearby message, and a contact information exchange message.

In Example 7, the subject matter of any one of Examples 1-6 can optionally include the logic being configured to: remove the communication alert in the first display screen when the input data to view the information associated with the communication is received.

In Example 8, the subject matter of any one of Examples 1-7 can optionally include human-readable information not being displayed in the first display screen with the graphic design.

In Example 9, the subject matter of any one of Examples 1-8 can optionally include a motion sensor being configured to detect the screen transition input to view the information associated with the communication, where the screen transition input corresponds to a particular movement, detectable by the motion sensor, of the wearable electronic device.

In Example 10, the subject matter of any one of Examples 1-9 can optionally include the logic being configured to: receive second input data when the information is displayed in the second display screen, the second input data indicative of a second screen transition input to view response options, where the second screen transition input is detectable by an input device that is not configured to detect the first screen transition input; and display one or more response options in the second display screen.

In Example 11, the subject matter of any one of Examples 1-10 can optionally include the first display screen and the second display screen forming a single display screen.

In Example 12, the subject matter of any one of Examples 1-10 can optionally include the first display screen being physically distinct from the second display screen.

In Example 13, the subject matter of any one of Examples 1-12 can optionally include a strap portion coupled to the display screen; and a latch portion to secure opposite ends of the strap portion together, where the logic comprises at least one processor.

In Example 14, the subject matter of any one of Examples 1-13 can optionally include the communication corresponding to an original communication sent to a mobile electronic device associated with the wearable electronic device.

In Example 15, the subject matter of any one of Examples 1 and 7-14 can optionally include the graphic design being one of a plurality of graphic designs each having a different notification pattern, where each notification pattern indicates a different type of the communication.

In Example 16, the subject matter of any one of Examples 1 and 7-14 can optionally include the graphic design being one of a plurality of graphic designs each having a different notification pattern, where each notification pattern indicates a different combination of one or more attributes of the communication.

Example 17 is at least one computer readable storage medium comprising instructions for a mobile electronic device that, when executed by at least one processor, cause the at least one processor to: provide a communication alert for display in a first display screen of the mobile electronic device, where the communication alert is a graphic design that represents a communication received by the mobile electronic device; receive input data indicative of screen transition input to view information associated with the communication; and provide human-readable information associated with the communication for display in a second display screen.

In Example 18, the subject matter of Example 17 can optionally include the instructions, when executed by the at least one processor, causing the processor to: select the communication alert to be displayed, where the graphic design includes a notification pattern indicating one or more attributes of the communication.

In Example 19, the subject matter of Example 18 can optionally include one of the attributes being a type of the communication, where the type is one of a plurality of types of communication.

In Example 20, the subject matter of any one of Examples 18-19 can optionally include the notification pattern being animated.

In Example 21, the subject matter of any one of Examples 18-20 can optionally include one of the attributes being one of a level of importance of a sender of the communication and a level of urgency of the communication.

In Example 22, the subject matter of Example 19 can optionally include the types of communication including one or more of a phone call message, a text message, an electronic mail message, an event or schedule message, a social network message, a social offer message, a friend nearby message, and a contact information exchange message.

In Example 23, the subject matter of any one of Examples 17-22 can optionally include the instructions, when executed by the at least one processor, causing the processor to: remove the communication alert in the first display screen when the input data to view the information associated with the communication is received.

In Example 24, the subject matter of any one of Examples 17-23 can optionally include human-readable information not being displayed in the first display screen with the graphic design.

In Example 25, the subject matter of any one of Examples 17-24 can optionally include a motion sensor being configured to detect the screen transition input to view the information associated with the communication, where the screen transition input corresponds to a particular movement, detectable by the motion sensor, of the wearable electronic device.

In Example 26, the subject matter of any one of Examples 17-25 can optionally include the instructions, when executed by the at least one processor, causing the processor to: receive second input data when the information is displayed in the second display screen, the second input data indicative of a second screen transition input to view response options, where the second screen transition input is detectable by an input device that is not configured to detect the first screen transition input; and display one or more response options in the second display screen.

In Example 27, the subject matter of any one of Examples 17-26 can optionally include the first display screen and the second display screen forming a single display screen.

In Example 28, the subject matter of any one of Examples 17-26 can optionally include the first display screen being physically distinct from the second display screen.

In Example 29, the subject matter of any one of Examples 17-28 can optionally include the communication corresponding to an original communication sent to another mobile electronic device associated with the mobile electronic device.

In Example 30, the subject matter of any one of Examples 17 and 23-29 can optionally include the graphic design being one of a plurality of graphic designs each having a different notification pattern, where each notification pattern indicates a different type of the communication.

In Example 31, the subject matter of any one of Examples 17 and 23-29 can optionally include the graphic design being one of a plurality of graphic designs each having a different notification pattern, where each notification pattern indicates a different combination of one or more attributes of the communication.

Example 32 is a method for a mobile electronic device, comprising: providing a communication alert for display in a first display screen of the mobile electronic device, where the communication alert is a graphic design that represents a communication received by the mobile electronic device; receiving input data indicative of screen transition input to view information associated with the communication; and providing human-readable information associated with the communication for display in a second display screen based.

In Example 33, the subject matter of Example 32 can optionally include selecting the communication alert to be displayed, where the graphic design includes a notification pattern indicating one or more attributes of the communication.

In Example 34, the subject matter of Example 33 can optionally include one of the attributes being a type of the communication, where the type is one of a plurality of types of communication.

In Example 35, the subject matter of any one of Examples 33-34 can optionally include the notification pattern being animated.

In Example 36, the subject matter of any one of Examples 33-35 can optionally include one of the attributes being one of a level of importance of a sender of the communication and a level of urgency of the communication.

In Example 37, the subject matter of any one of Examples 34 can optionally include the types of communication including one or more of a phone call message, a text message, an electronic mail message, an event or schedule message, a social network message, a social offer message, a friend nearby message, and a contact information exchange message.

In Example 38, the subject matter of any one of Examples 32-37 can optionally include removing the communication alert in the first display screen when the input data to view the information associated with the communication is received.

In Example 39, the subject matter of any one of Examples 32-38 can optionally include human-readable information not being displayed in the first display screen with the graphic design.

In Example 40, the subject matter of any one of Examples 32-39 can optionally include a motion sensor being configured to detect the screen transition input to view the information associated with the communication, where the screen transition input corresponds to a particular movement, detectable by the motion sensor, of the wearable electronic device.

In Example 41, the subject matter of any one of Examples 32-40 can optionally include receiving second input data when the information is displayed in the second display screen, the second input data indicative of a second screen transition input to view response options, where the second screen transition input is detectable by an input device that is not configured to detect the first screen transition input; and displaying one or more response options in the second display screen.

In Example 42, the subject matter of any one of Examples 32-41 can optionally include the first display screen and the second display screen forming a single display screen.

In Example 43, the subject matter of any one of Examples 32-41 can optionally include the first display screen being physically distinct from the second display screen.

In Example 44, the subject matter of any one of Examples 32-43 can optionally include the communication corresponding to an original communication sent to another mobile electronic device associated with the mobile electronic device.

In Example 45, the subject matter of any one of Examples 32 and 38-44 can optionally include the graphic design being one of a plurality of graphic designs each having a different notification pattern, where each notification pattern indicates a different type of the communication.

In Example 46, the subject matter of any one of Examples 32 and 38-44 can optionally include the graphic design being one of a plurality of graphic designs each having a different notification pattern, where each notification pattern indicates a different combination of one or more attributes of the communication.

Example 47 is a system, comprising a wearable electronic device; a display screen coupled to the wearable electronic device; and logic, at least a portion of which is implemented in hardware, the logic configured to: receive a communication over a wireless network; display, in the display screen, a communication alert representing the communication, wherein the communication alert is a graphic design; receive input data indicative of a screen transition input to view information associated with the communication; and display, in the display device, the information associated with the communication.

In Example 48, the subject matter of Example 47 can optionally include the display screen comprising a first display screen for displaying the communication alert; and a second display screen for displaying the information associated with the communication, where the first and second display screens are physically distinct.

In Example 49, the subject matter of any one of Examples 47-48 can optionally include at least one processor and at least one memory element.

Example 50 is an apparatus for protecting data, comprising means for performing the method of any one of claims 32-46.

In Example 51, the subject matter of Example 50 can optionally include the means for performing the method comprising at least one processor and at least one memory element.

In Example 52, the subject matter of Example 51 can optionally include the at least one memory element comprising machine readable instructions that when executed, cause the apparatus to perform the method of any one of claims 32-46.

In Example 53, the subject matter of any one of Examples 50-52 can optionally include the apparatus being a wearable electronic device.

What is claimed is:
1. A wearable electronic device, comprising:
a strap portion;
a first display screen coupled to the strap portion;
a second display screen coupled to the strap portion, wherein the first display screen and the second display screen are separated by a spacing longitudinally defined along the strap portion such that the first display screen and the second display screen are disposed on opposite sides of a wrist when the strap portion is secured around the wrist; and
logic, at least a portion of which is implemented in hardware, the logic configured to:
receive a communication over a wireless network;
display, in the first display screen, a communication alert representing the communication, wherein the communication alert is a graphic design;

receive input data indicative of a screen transition input to view information associated with the communication; and display, in the second display screen, the information associated with the communication.

2. The wearable electronic device of claim 1, wherein the logic is configured to:

select the communication alert to be displayed, wherein the graphic design includes a notification pattern indicating one or more attributes of the communication.

3. The wearable electronic device of claim 2, wherein one of the attributes is a type of the communication, wherein the type is one of a plurality of types of communication.

4. The wearable electronic device of claim 3, wherein the types of communication include one or more of a phone call message, a text message, an electronic mail message, an event or schedule message, a social network message, a social offer message, a friend nearby message, and a contact information exchange message.

5. The wearable electronic device of claim 2, wherein the notification pattern is animated.

6. The wearable electronic device of claim 2, wherein one of the attributes is one of a level of importance of a sender of the communication and a level of urgency of the communication.

7. The wearable electronic device of claim 1, wherein the logic is configured to:

remove the communication alert in the first display screen when the input data to view the information associated with the communication is received.

8. The wearable electronic device of claim 1, wherein human-readable information is not displayed in the first display screen with the graphic design.

9. The wearable electronic device of claim 1, wherein a motion sensor is configured to detect the screen transition input to view the information associated with the communication, wherein the screen transition input corresponds to a particular movement, detectable by the motion sensor, of the wearable electronic device.

10. The wearable electronic device of claim 1, wherein the logic is configured to:

receive second input data when the information is displayed in the second display screen, the second input data indicative of a second screen transition input to view response options, wherein the second screen transition input is detectable by an input device that is not configured to detect the first screen transition input; and display one or more of the response options in the second display screen.

11. The wearable electronic device of claim 1, further comprising:

a latch portion to secure opposite ends of the strap portion together, wherein the logic comprises at least one processor.

12. The wearable electronic device of claim 1, wherein the communication corresponds to an original communication sent to a mobile electronic device associated with the wearable electronic device.

13. The wearable electronic device of claim 1, wherein the strap portion includes:

first and second ends; and a latch portion configured to releasably couple the first and second ends together.

14. The wearable electronic device of claim 1, wherein the first and second display screens are disposed along the strap portion such that, when the strap portion is secured to a human wrist, the first display screen is positioned adjacent a top side of the human wrist if the second display screen is positioned adjacent a bottom side of the human wrist.

15. At least one non-transitory computer readable storage medium comprising instructions for a mobile electronic device that, when executed by at least one processor, cause the at least one processor to:

provide a communication alert for display in a first display screen of the mobile electronic device, wherein the communication alert is a graphic design that represents a communication received by the mobile electronic device;

receive input data indicative of screen transition input to view information associated with the communication; and provide human-readable information associated with the communication for display in a second display screen, wherein the first and second display screens are coupled to a strap portion, wherein the first display screen and the second display screen are separated by a spacing longitudinally defined along the strap portion such that the first display screen and the second display screen are disposed on opposite sides of a wrist when the strap portion is secured around the wrist.

16. The at least one non-transitory computer readable storage medium of claim 15, wherein the instructions, when executed by the at least one processor, cause the processor to:

determine the communication alert to be displayed, wherein the graphic design includes a notification pattern indicating one or more attributes of the communication.

17. The at least one non-transitory computer readable storage medium of claim 15, wherein the instructions, when executed by the at least one processor, cause the processor to:

remove the communication alert in the first display screen when the input data to view the information associated with the communication is received.

18. The at least one non-transitory computer readable storage medium of claim 15, wherein human-readable information is not displayed in the first display screen with the graphic design.

19. The at least one non-transitory computer readable storage medium of claim 15, wherein the instructions, when executed by the at least one processor, cause the processor to:

receive second input data when the information is displayed in the second display screen, the second input data indicative of a second screen transition input to view response options, wherein the second screen transition input is detectable by an input device that is not configured to detect the first screen transition input; and display one or more response options in the second display screen.

20. A method for a mobile electronic device, comprising:

providing a communication alert for display in a first display screen of the mobile electronic device, wherein the communication alert is a graphic design that represents a communication received by the mobile electronic device;

receiving input data indicative of screen transition input to view information associated with the communication; and providing human-readable information associated with the communication for display in a second display screen, wherein the first and second display screens are coupled to a strap portion, and wherein the first display screen and the second display screen are separated by a spacing longitudinally defined along the strap portion such that the first display screen and the second display screen are disposed on opposite sides of a wrist w the strap portion is secured around the wrist.

21. The method of claim 20, wherein the communication corresponds to an original communication sent to another mobile electronic device associated with the mobile electronic device.

22. The method of claim 20, wherein the graphic design is one of a plurality of graphic designs each having a different notification pattern, wherein each notification pattern indicates a different combination of one or more attributes of the communication.

23. A system, comprising:
   a wearable electronic device including a strap portion;
   a first display screen coupled to the strap portion of the wearable electronic device;
   a second display screen coupled to the strap portion of the wearable electronic device, wherein the first display screen and the second display screen are separated by a spacing longitudinally defined along the strap portion such that the first display screen and the second display screen are disposed on opposite sides of a wrist when the strap portion is secured around the wrist; and
   logic, at least a portion of which is implemented in hardware, the logic configured to:
      receive a communication over a wireless network;
      display, in the first display screen, a communication alert representing the communication, wherein the communication alert is a graphic design;
      receive input data indicative of a screen transition input to view information associated with the communication; and
      display, in the second display device, the information associated with the communication.

24. The system of claim 23, further comprising:
   at least one processor; and
   at least one memory element.

* * * * *

UNITED STATES PATENT AND TRADEMARK OFFICE
CERTIFICATE OF CORRECTION

PATENT NO. : 9,448,755 B2
APPLICATION NO. : 14/142841
DATED : September 20, 2016
INVENTOR(S) : Mark R. Francis et al.

It is certified that error appears in the above-identified patent and that said Letters Patent is hereby corrected as shown below:

In the Claims

In column 33, line 6, in Claim 20, delete "wrist w" and insert -- wrist when --, therefor.

Signed and Sealed this
Twenty-ninth Day of November, 2016

Michelle K. Lee
*Director of the United States Patent and Trademark Office*